United States Patent
Gardeski et al.

(10) Patent No.: US 7,338,481 B2
(45) Date of Patent: Mar. 4, 2008

(54) SLITTING TOOL

(75) Inventors: Kenneth C. Gardeski, Plymouth, MN (US); Jeff J. Jannicke, Andover, MN (US); Stanten C. Spear, Arden Hills, MN (US); David A. Schuelke, Stillwater, MN (US); Debbie L. Kirihara, St. Louis Park, MN (US); Elizabeth A. Ellingson, Eden Prairie, MN (US); Jeremy J. Odegard, River Falls, WI (US); Richard P. Manahan, Lake Elmo, MN (US); Andrzej M. Malewicz, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 266 days.

(21) Appl. No.: 10/367,420

(22) Filed: Feb. 14, 2003

(65) Prior Publication Data

US 2003/0181935 A1  Sep. 25, 2003

Related U.S. Application Data

(63) Continuation-in-part of application No. 10/078,026, filed on Feb. 15, 2002, now Pat. No. 7,029,460.

(51) Int. Cl.
*A61M 25/00* (2006.01)
*A61M 31/00* (2006.01)

(52) U.S. Cl. .................... 604/524; 604/95; 604/510

(58) Field of Classification Search ........ 604/161–500, 604/510, 524–527, 95
See application file for complete search history.

(56) References Cited

U.S. PATENT DOCUMENTS

| | | | |
|---|---|---|---|
| 2,141,002 A | 12/1938 | Huff | |
| 3,902,501 A | 9/1975 | Citron et al. | |
| 4,394,828 A | 7/1983 | Garbis et al. | |
| 4,631,059 A | 12/1986 | Wolvek et al. | |
| 4,687,469 A * | 8/1987 | Osypka | 604/161 |
| 4,997,424 A | 3/1991 | Little | |
| 5,188,606 A | 2/1993 | Maloney et al. | |
| 5,261,887 A | 11/1993 | Walker | |
| 5,330,460 A * | 7/1994 | Moss et al. | 30/90.4 |
| 6,159,198 A | 12/2000 | Gardeski et al. | |
| 6,497,681 B1 * | 12/2002 | Brenner | 604/164.05 |

* cited by examiner

*Primary Examiner*—Vy Q. Bui
(74) *Attorney, Agent, or Firm*—Michael C. Soldner; Carol F. Barry; Steve Bauer

(57) ABSTRACT

A slitting tool for severing a tubular body includes a body portion, extending along a first axis, joined to a nose portion extending along a second axis, the second axis extending at an angle between approximately 5 degrees and approximately 90 degrees with respect to the first axis. The nose portion includes means for severing the tubular body while the body portion includes means for gripping by a hand of a user such that a wrist of the hand is in a neutral position when the means for severing is directed toward the tubular body.

21 Claims, 21 Drawing Sheets

SLITTING TOOL

PRIORITY CLAIM

This application is a continuation-in-part of U.S. patent application Ser. No. 10/078,026, filed Feb. 15, 2002, now U.S. Pat. No. 7,029,460 entitled "Improved Slitting Tool" which is incorporated herein by reference in its entirety.

FIELD OF THE INVENTION

The current invention relates to an improved tool for slitting a delivery sheath or introducer; and more particularly, relates to an ergonomic slitting tool.

BACKGROUND OF THE INVENTION

Delivery sheaths and medical electrical leads are often inserted into a patient's body by means of introducer systems. These introducer systems typically include an elongated sheath which is inserted into the blood vessel or other portion of the patient's body. A delivery sheath or lead may then be introduced through a lumen of the introducer. In those circumstances in which the lead or delivery sheath is to remain in the patient's body for a considerable period of time, it is desirable to be able to remove the introducer sheath without removing the lead or delivery sheath.

Another related procedure involves placing a lead at a target destination through a lumen of a delivery sheath. After the lead is in position, the delivery sheath must be removed from the body while leaving the lead undisturbed. If the lead is coupled to an isodiametric connector that is substantially the same size as the lead body, the delivery sheath can be removed from the body by pulling the delivery sheath over the connector. Many connectors, however, are larger than the lead body so that the delivery sheath cannot be withdrawn over the connector, and some other means of removal must be employed.

One commonly employed mechanism for removing an introducer sheath or a delivery sheath from around another device is to provide the sheath or delivery sheath with weakened zones so that it can be torn or split and thereby removed from around the encircled device. One introducer system employing this mechanism is illustrated in U.S. Pat. No. 5,409,469 issued to Scheaerf, incorporated herein by reference in its entirety.

Another commonly employed mechanism for removing a sheath or delivery sheath from around a delivery sheath or lead is to simply slit the sheath along its length as it is pulled proximally along the inner lead or delivery sheath and out of the patient's body. Various exemplary slitter designs are disclosed in U.S. Pat. No. 4,997,424 issued to Little, U.S. Pat. No. 6,159,198 issued to Gardeski, and U.S. Pat. No. 5,330,460 to Moss et al. These prior art designs include mechanisms that grasp or otherwise couple to a lead or catheter body. For example, the '424 patent to Little describes a slitter that includes an arcuate section having an inner peripheral wall that extends arcuately through an angle of at least about 180 degrees, and which is adapted to abut against a delivery sheath while an introducer tube is slit away from the catheter body.

Because prior art slitter tools are adapted to couple to the inner lead or catheter body while the encircling introducer or delivery sheath is being slit away, the dimensions of the slitter tool must be tailored for a particular lead or delivery sheath. For example, a slitting tool adapted to couple to a 4 French lead will not properly attach to a 2 French lead, and so on. As a result, pre-packaged lead, delivery sheath, or introducer kits must be provided with specific slitting tools sized for use with the devices in the kit, increasing manufacturing costs and inventory.

Another problem associated with the coupling mechanisms of prior art slitting tools involves difficulties with deployment. Prior art clamping mechanisms add unnecessary bulk and complexity to the slitter. Moreover, such tools may attach to a lead body in a manner that is not intuitive. As a result, the user may incorrectly couple the slitter to the lead body, and the outer surface of the lead may therefore be damaged during the slitting process.

Yet another difficulty with using prior art slitting tools has to do with lead dislodgement. The coupling mechanisms provided by prior art slitting tools could suddenly disengage from a lead during the slitting process. This may cause the lead body to abruptly move in a manner that dislodges the lead distal tip. As a result, the lead placement procedure must be repeated, resulting in additional trauma to the patient.

Another disadvantage with prior art slitting tools is that they are not designed ergonomically. For example, most prior art tools are adapted to be grasped by the user with the index finger and thumb in the general plane of the cutting blade. In this case, the reactionary force causing by the slitting process is resisted by squeezing the slitter between the index finger and the thumb, which does not provide good support. Moreover, many tools of this type require the palm of the hand to be generally facing in an upward direction, which tends to be unstable. Finally, grasping a slitting tool in this manner encourages the user to incorrectly push the slitter toward the delivery sheath rather than to pull the delivery sheath past the slitter in the correct manner of use. As a result, the slitting process is made much more difficult, and potential damage to the inner device may occur.

What is needed, therefore, is an improved slitting tool that addresses the forgoing problems.

DETAILED DESCRIPTION OF THE INVENTION

Figure 1:
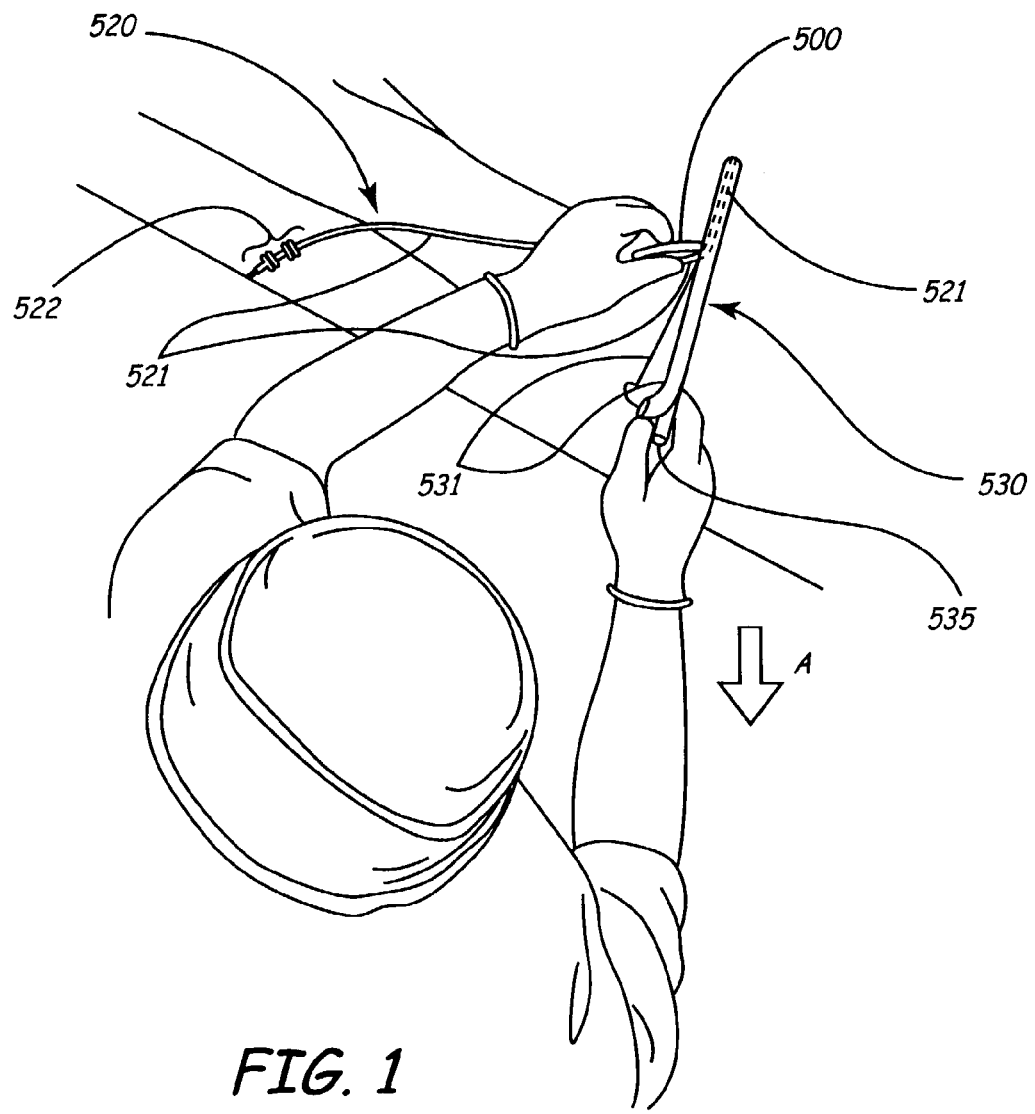
FIG. 1 is a schematic overhead view of a user slitting a delivery sheath with one embodiment of a slitting tool according to the present invention.

FIG. 1 is a schematic overhead view of a user slitting a delivery sheath 530 with one embodiment of a slitting tool 500 according to the present invention. As illustrated in FIG. 1, the user is slitting delivery sheath 530 from around an electrical lead 520 including a lead body 521 and a connector 522. Delivery sheath 530 has been inserted into a patients venous system to serve as a conduit for delivery of lead 520 into the patient's heart. Once lead 520 has been implanted, delivery sheath 530 needs to be removed. According to the present invention delivery sheath 530 is peeled from around lead body 521 by slitting a wall 531 of delivery sheath 530 with slitting tool 500. Although an electrical lead is illustrated in FIG. 1, slitting tool 500 may be used to facilitate removal of a sheath from around any implantable medical device that includes an elongated body, examples of which include catheters designed to delivery other therapies besides electrical therapy. As illustrated in FIG. 1, delivery sheath 530 includes a handle 535, which is grasped by a first hand of the user who pulls sheath 530 in a direction according to arrow 'A'. As further illustrated in FIG. 1, a second hand grasps lead body 521 and slitting tool 500, holding both steady, while sheath 530 is pulled against a cutting edge (not shown) of slitting tool 500. According to the present invention slitting tool 500 may be grasped for slitting such that a wrist for the second hand of the user is in a neutral position promoting control during the slitting operation; a neutral position being defined herein as a position that is not contorted or hyper-extended.

Figure 2:
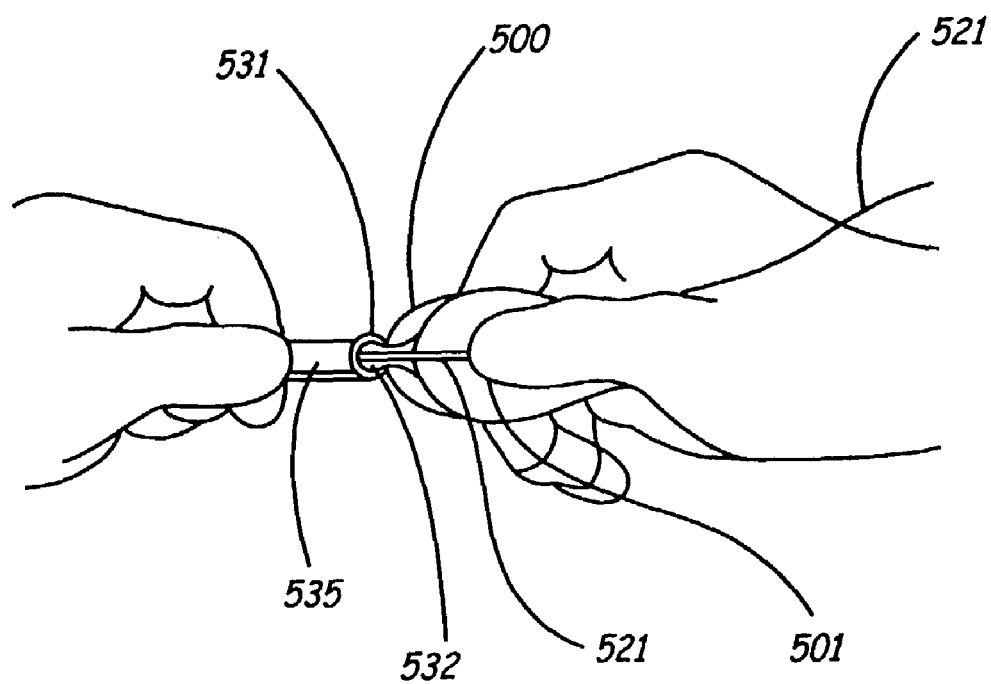
FIG. 2 is a schematic end view of a user slitting a delivery sheath with the slitting tool shown in FIG. 1.

FIG. 2 is a schematic end view of the user slitting delivery sheath 530 with slitting tool 500. As illustrated in FIG. 2, the first hand of the user is grasping handle 535 of delivery sheath 530 while the second hand is directing the cutting edge (not shown) of slitting tool 500 toward delivery sheath wall (into the page) 531 and grasping lead body 521 between an outer surface 501 of slitting tool 500. According to the current invention, slitting tool 500 and all the various embodiments described herein provide an intuitive way to grip and maintain the slitting tool against a lead body, such as lead body 521, or a catheter body, while holding slitting tool steady. Because a thumb ensures a fixed relationship between slitting tool 500 and lead body 521, or a catheter body, a user is not inclined to push slitting tool 500 against delivery sheath wall 531 rather than pull delivery sheath wall 531 against the cutting edge of a slitting tool 500.

Figure 3:
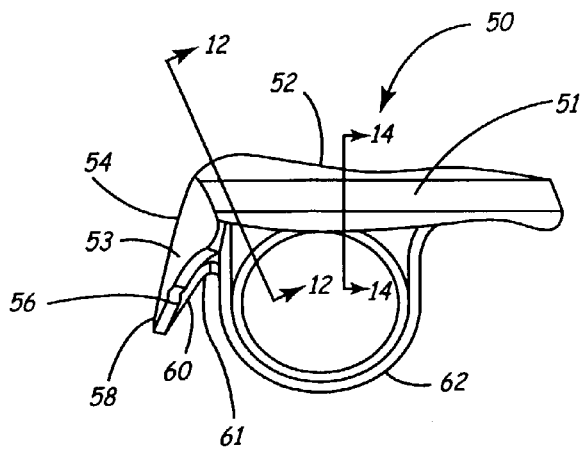
FIG. 3 is a side plan view of one embodiment of a slitting tool according to the current invention.

FIG. 3 is a side plan view of one embodiment of a slitting tool 50 according to the current invention. This embodiment includes a body 51 having a top surface 52. Body 51 is coupled to a nose section 53. Nose section has a front surface 54, and an inner surface 56. Front surface 54 and inner surface 56 intersection at a tip portion 58. Inner surface 56 is coupled to a cutting member 60 such as a blade. Body 51 of the current embodiment includes a ring-like gripping member 62 to aid in grasping slitting tool 50, and to protect the fingers from cutting member 60. Any other shape or size gripping mechanism may be utilized in the alternative, and the ring is merely exemplary.

As shown in FIG. 3, the cutting member 60 of one embodiment has a shallow angle of between 15 and 45 degrees with respect to the tubular body being slit. In a particular embodiment, the cutting member has a blade angle of approximately 30 degrees when measured from the front surface. This angle is more shallow than in prior art cutting tools generally having blades angled at 60 degrees or more. A more shallow angle results in a smoother cutting action with an approximately ten percent lower slitting force.

It may further be noted that the cutting member 60 shown in FIG. 3 has a curved cutting edge portion 61 with a sawtooth configuration. This portion of the blade is particularly effective in cutting through a slittable hub located at the proximal end of many delivery sheaths. The apex of the blade is shaped to receive the conical taper of the hub and to stabilize the slitter prior to, and during, the hub slitting process. The apex of the blade can be further optimized in shape and position to slit the shaft of introducer sheaths and delivery sheaths. In this latter case, the apex is more pointed and moved distal toward the tip portion 58 and closer to the front surface.

Figure 4A:
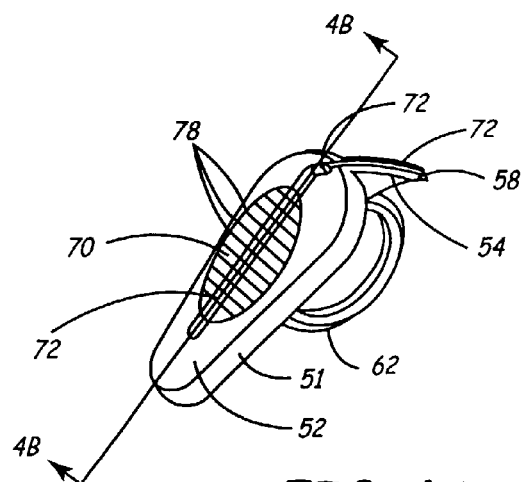
FIG. 4A is a top perspective view of the slitting tool of FIG. 3.

FIG. 4A is a top perspective view of slitting tool 50. This view shows a recessed area 70 on top surface 52. Recessed area is adapted to receive a thumb of either hand when slitting tool 50 is being grasped by a user during a slitting operation. It may be noted that in another embodiment wherein the orientation of recessed area is changed within respect to the body of the slitting tool, recessed area could be adapted to receive a finger other than the thumb. This recessed area may have textured ridges 78 of any other type of texturing in the manner shown to allow for an enhanced grip. For example, texturing could be provided by surface treating recessed area 70 using a plasma etching, chemical milling, or ion bombardment process.

Top surface 52 further includes a channel 72 that extends along at least a portion of top surface, and further continues along at least a portion of front surface 54 of nose section 53. In the embodiment shown, channel 72 runs the entire length of nose section 53 to tip portion 58. This channel is provided to align a lead, delivery sheath, or body of another implantable device in relation to the delivery sheath and slitter, but does not clamp or affix to the lead. The lead is instead held in place by the user's thumb positioned within recessed area in a manner to be discussed further below. Channel 72 may be semi-circular, may form a "V" or a "U", may have a stepped surface, or may be formed in another shape. In addition, the surface of channel 72 may be textured or smooth. Texturing may be provided using any means known in the art, including those discussed in the foregoing paragraph. Providing channel 72 with a textured surface helps to prevent relative movement of a lead, delivery sheath, or other IMD in relation to the slitting tool without the use of a clamping or affixing mechanism. In one embodiment, channel 72 extends through an angle of less than 180 degrees. In a particular embodiment, the channel ranges from 40 to 160 degrees.

Figure 4B:
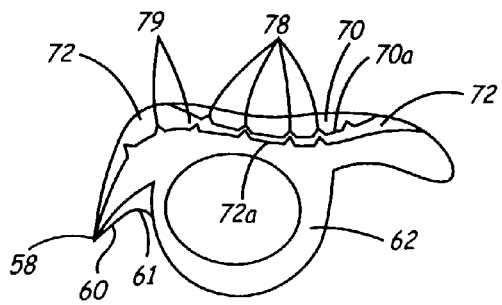
FIG. 4B is a cross-sectional view along line 4B-4B of FIG. 4A.

FIG. 4B is a cross-sectional view of slitting tool 50 along line 4B-4B of FIG. 4A. This view illustrates an embodiment wherein the bottom surface 72a of channel 72 includes texturing 79 in the manner discussed above. Bottom surface 70a of recessed area 70 also includes texturing 78.

Figure 5:
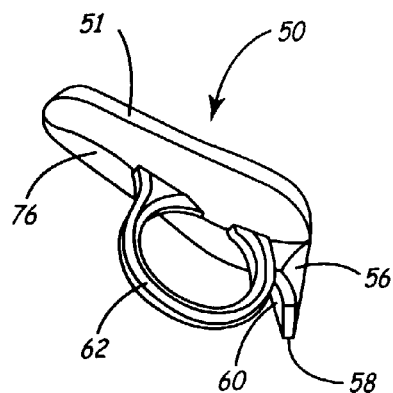
FIG. 5 is a bottom perspective view of the slitting tool of FIG. 3.

FIG. 5 is a bottom perspective view of slitting tool 50. This view further illustrates gripping member 62, and a bottom surface 76 of slitting tool.

Figure 6:
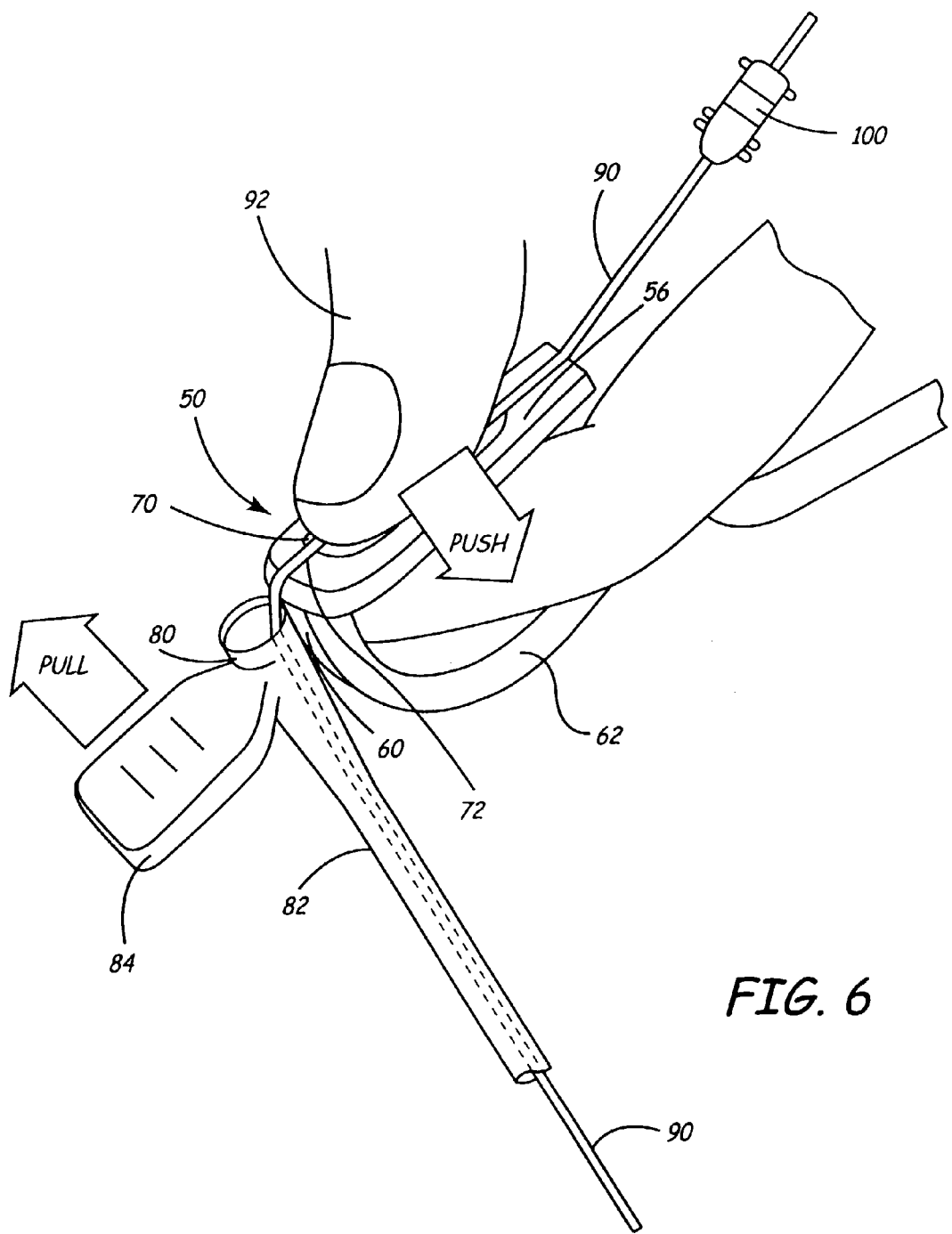
FIG. 6 is a perspective side view of the slitting tool of FIG. 3 engaging a hub of a delivery sheath.

FIG. 6 is a perspective side view of slitting tool 50 engaging a hub 80 of a delivery sheath 82. Only a proximal portion of delivery sheath 82 is shown. A lead 90 (shown partially dashed) is positioned within an inner lumen of delivery sheath 82, with a proximal end extending beyond proximal end of the delivery sheath. The proximal portion of the lead is positioned within channel 72. Because of the size of the channel, only a portion of the lead 90 resides within channel 72. A thumb 92 of user may be placed over the lead, with pressure applied in a downward direction. This force maintains lead 90 against top surface 52 within recessed area 70.

In one embodiment of the invention, channel 72 is deeper at the top of nose section 53 where top surface 52 and front surface 54 intersect. In this region, channel 72 may be deep enough to receive the entire body of the lead 90. This protects lead 90 from the sharp slit edge of the delivery sheath during the slitting process. This deeper portion of the channel also helps retain the lead prior to positioning a finger within recessed area.

Slitting tool 50 is used by pulling a handle 84 of delivery sheath 82 toward the user and over cutting member 60. Severing delivery sheath 82 in this manner allows the delivery sheath to be removed from around lead 90, since connector assembly 100 is too large to allow delivery sheath to be retracted over the connector. Channel 72 in the top of nose section 53 supports lead 90 and redirects it so that it does not contact a sharp severed edge of delivery sheath 82. This portion of channel 72, transitioning from nose section 53 to top surface 52, is typically constructed deeper to protect the lead from being damaged during the slitting operation. This view further shows the manner in which a pushing force applied by the hand gripping slitting tool will be opposed by an opposite pulling force asserted by another hand that is gripping hub 80 of delivery sheath 82.

Figure 7:
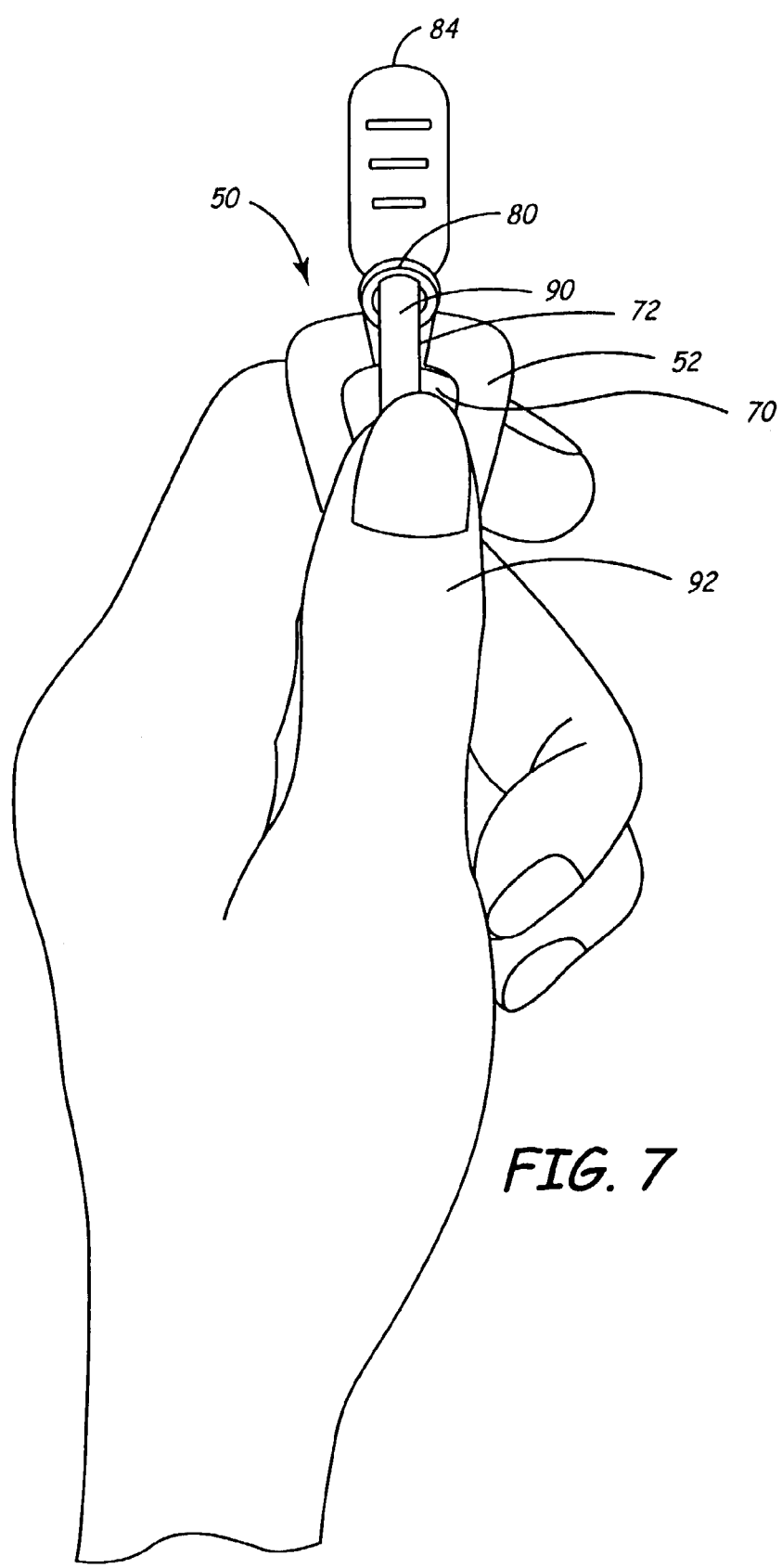
FIG. 7 is a top view of the slitting tool of FIG. 3 illustrating one manner of use.

FIG. 7 is a top view of slitting tool 50 illustrating one manner of using the tool. A portion of lead 90 is positioned within channel 72, which is shown extending into recessed area 70 of top surface 52. Thumb 92 of user is positioned over recessed area 70 and channel 72 to hold lead 90 in position. This view further illustrates that cutting tool may be gasped with the palm of the user's hand facing inward toward the user's body and a slightly downward direction. Moreover, the current tool need not be grasped with the thumb and forefinger positioned within the general plane of the cutting blade. This is a more comfortable orientation than prior art designs. Additionally, the manner of grasping the tool provides for better stability and user control.

Figure 8:
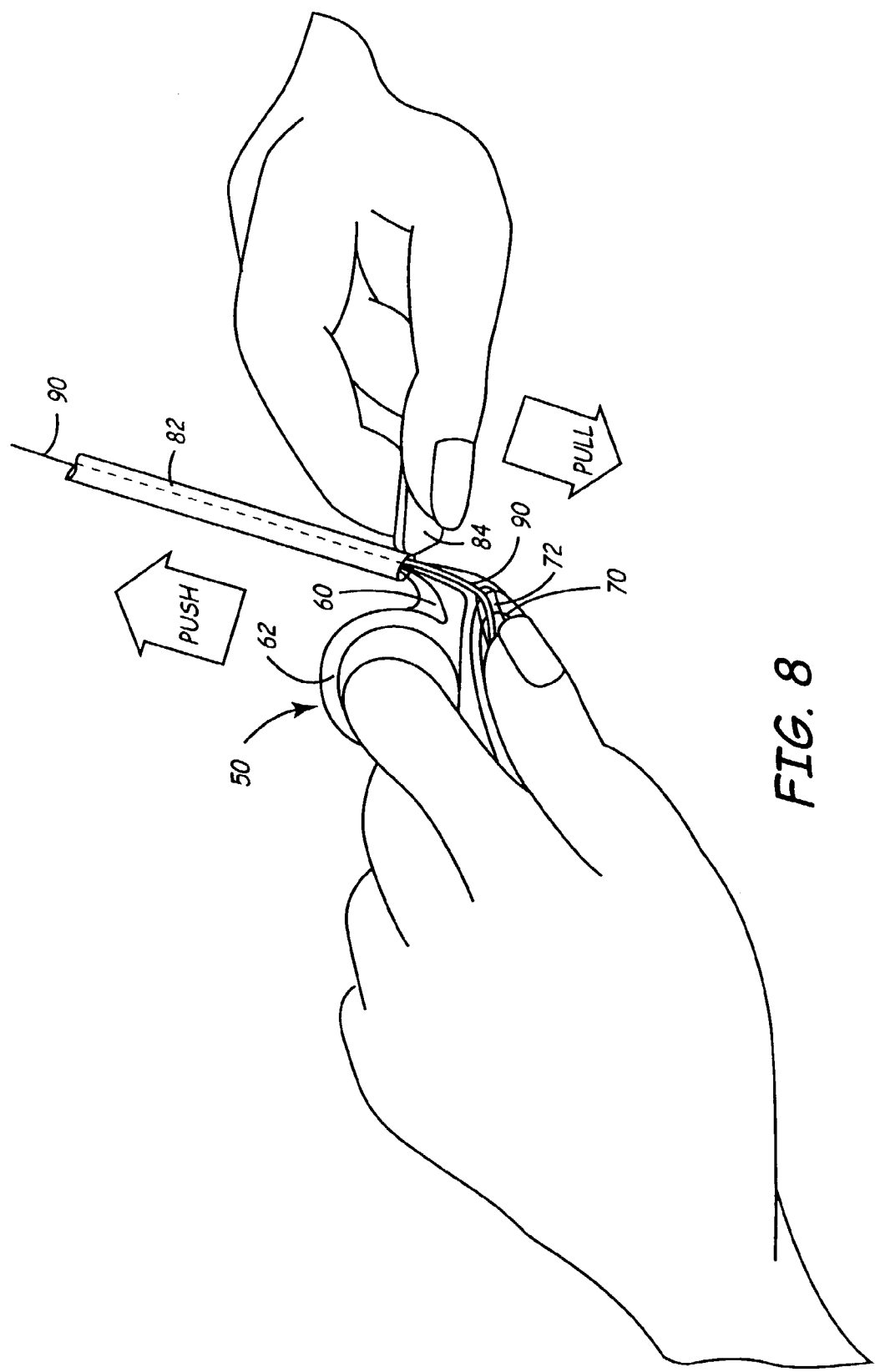
FIG. 8 is a side view of the slitting tool of FIG. 3 illustrating another manner of use.

FIG. 8 is a side view of slitting tool 50 illustrating another manner of use. This figure illustrates the manner in which the hand gripping the slitting tool asserts a pushing force that is opposed by the other hand gripping a handle 84 of the delivery sheath 82. In this view, the user performs slitting action with the palm of the hand facing in a generally downward direction. The current invention may be used in this manner or in the manner discussed above based on user preference, patient orientation, and user characteristics which may include the user's height. Further, slitting tool may be used by either a left or right hand. Finally, one skilled in the art will appreciate that slitting tool may be adapted for use with a finger other than a thumb by positioning recessed area and channel on another surface of the slitting tool 50.

Figure 9:
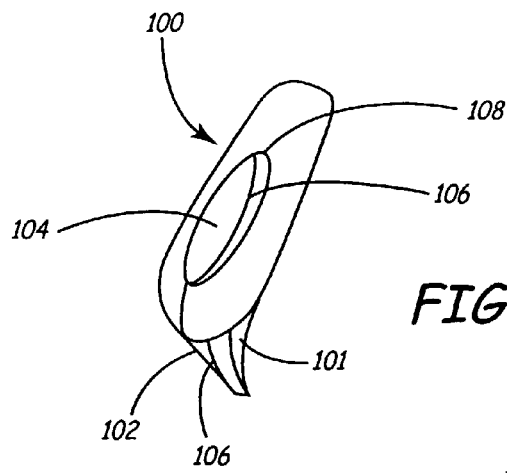
FIG. 9 is a top perspective view of another embodiment of the inventive slitting tool.

FIG. 9 is a top perspective view of another embodiment of the current invention. According to this embodiment, slitting tool 100 does not include gripping member 62 (FIGS. 1-8), and nose portion 102 is shorter than illustrated in previous embodiments. Slitting tool 100 includes a cutting member 101, a recessed area 104, and a channel 106, all of which are similar to aspects of the previous embodiment discussed above. In the current embodiment, channel 106 extends over a portion of top surface 108 and over the entire length nose portion 102.

Figure 10:
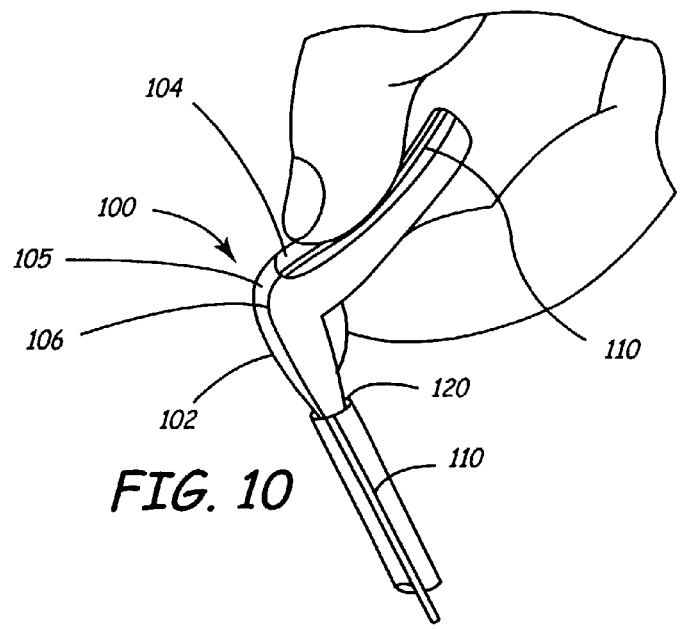
FIG. 10 is a side perspective view illustrating a manner of using the slitting tool of FIG. 9.

FIG. 10 illustrates a manner of using slitting tool 100. Thumb of user is positioned within recessed area 104, and holds a lead 110 in position within channel 106. Nose portion 102 is shown extending into delivery sheath 120 (shown cutaway), with nose portion 102 supporting lead 110 in preparation for slitting the delivery sheath. In this embodiment, channel has a maximum depth around top 105 of nose portion 102 such that lead 110 is barely visible in this region. This embodiment helps protect the lead in a manner discussed above.

Figure 11:
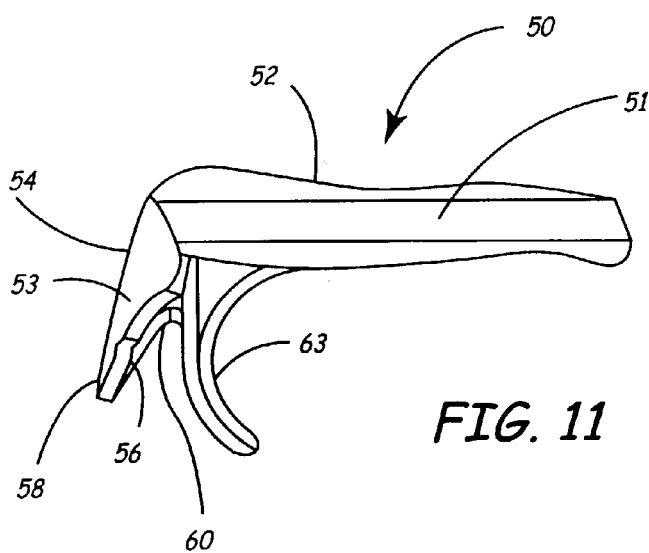
FIG. 11 is yet another embodiment of the current invention providing a guard member to protect the user from cutting member.

FIG. 11 is yet another embodiment of the current invention providing a guard member 63 to protect the user against cutting member 60. Other aspects of this embodiment similar to those shown in FIG. 3 are labeled with like numeric designators. Guard member 63 prevents fingers of a user from sliding forward and contacting cutting member 60. In one embodiment, guard member 63 may be a partial ring similar in shape and structure to gripping member 62 (FIG. 3.) In another embodiment, guard member 63 may take a different shape and/or size.

Many alternative embodiments of the current invention may be contemplated by one skilled in the art. For example, channel 72 may take any desired shape such as a generally "V" shaped channel, a "U" channel, a "stepped-V" or "stepped-U" channel, a combination thereof, or any other desired shape. The channel may extend over a portion, or all, of front surface 54 of nose section 53, and may extend over a portion, or all, of top surface 52. Channel may have a uniform shape, width and depth, or a shape and/or size that varies along the channel length. For example, the depth of channel may be at a maximum at the intersection of top surface 52 and front surface 54 in the manner discussed above. At this location, the shape may be a relatively deep "V" shape, with a more shallow rounded channel used elsewhere. Similarly, recessed area 70 may take many shapes and sizes, included stepped, rounded, or "V-shape"

surfaces, as noted above. Such constructions allow one slitting tool with one blade to accommodate several lead body diameters.

According to one aspect of the invention, a tacky overmolding material formed of a relatively low durometer polymer may be used to form all, or a portion, of the channel. A tacky channel surface minimizes relative movement of the slitting tool to the axis of the lead body or delivery sheath. In one exemplary embodiment, an aromatic polyurethane such as Thermedics Tecothane® TT-1074A, 75 Shore A durometer may be overlaid over a more rigid polyurethane such as DOW Isoplast™ 301 or DOW Pellethane® 2363-75D, which is used to form the body of the slitting tool. Texturing may be provided in the overmold surface, if desired.

Figure 12:
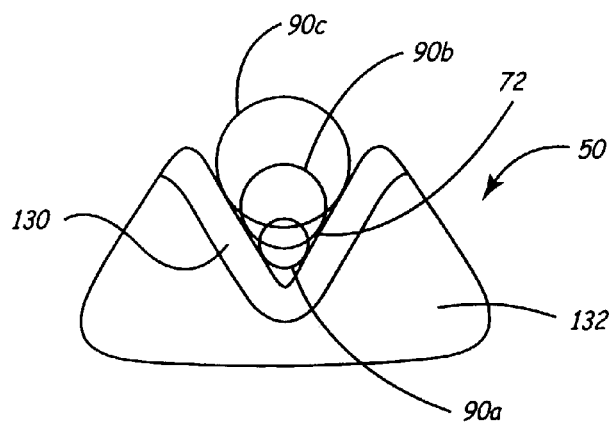
FIG. 12 is a cross-sectional view of the slitting tool of FIG. 3 along line 12-12.

FIG. 12 is a cross-sectional view of slitting tool 50 at line 12-12 of FIG. 3. As noted above, channel 72 may be of a non-uniform depth, and in one preferred embodiment, has a depth that is at a maximum at the intersection of top surface 52 and front surface 54 at the location roughly shown by line 12-12. In this embodiment, channel 72 is generally shaped as a "V", although a "U" or other type shape may be selected in the alternative. This view shows an optional overmolded area 130 that includes channel 72. The overmolding may be formed of the lower durometer, tacky polymer that adheres to the lead body, as described above. A harder material may be used to form the body 132 of the slitter. FIG. 12 illustrates the manner in which IMDs such as leads 90a, 90b, and 90c having varying diameters may be accommodated by the channel. In a preferred embodiment, the current invention accommodates IMDs having a diameter of between 2 and 8 French.

Figure 13:
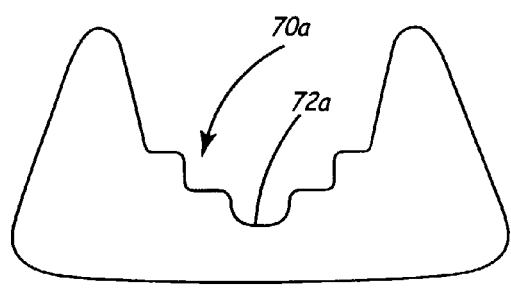
FIG. 13 is a cross-sectional view of another embodiment of the slitting tool at line 12-12 of FIG. 3.

FIG. 13 is a cross-sectional view of another embodiment of slitting tool 50 at line 12-12 of FIG. 3. In this embodiment, recessed area 70a is formed by a series of rounded steps designed to accommodate various lead and/or catheter body dimensions in a manner similar to that shown in FIG. 12. Channel 72a is a "U-shaped" groove at the bottom of recessed area. Although not shown, an overmolded area may be incorporated into the slitter in the manner discussed in reference to FIG. 12.

Figure 14:
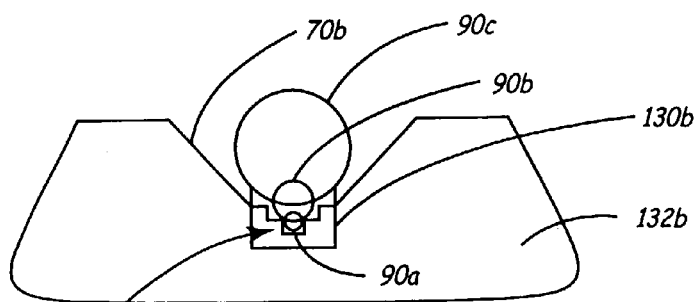
FIG. 14 is yet another cross-sectional view of an embodiment of slitting tool along line 14-14 of FIG. 3.

FIG. 14 is yet another cross-sectional view of an embodiment of slitting tool 50 at line 14-14 of FIG. 3. Recessed area 70b is a shallow "V-shape", with channel 72b being formed by a series of steps that are sized to accommodate IMDs such as leads 90a, 90b, and 90c having varying diameters. A softer overmold area 130b may be provided over the remainder of the slitter body 132b, as previously described. It may be noted that channel 72 may be deeper at the intersection of top surface 52 and front surface 54 than at the location of line 14-14 of FIG. 3. This is evident from comparing FIGS. 12 and 13 to FIGS. 14 and 15. Providing a deeper channel at the top of nose section 53 protects the lead in the manner discussed above.

Figure 15:
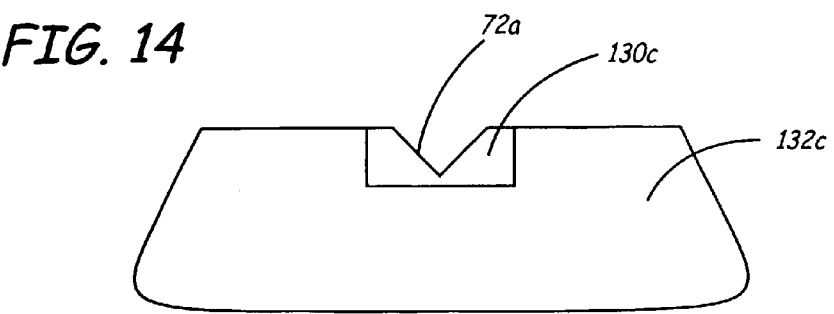
FIG. 15 illustrates an embodiment of slitter without a recessed area along line 14-14 of FIG. 3.

FIG. 15 illustrates an embodiment of slitter without recessed area 70 at line 14-14 of FIG. 3. In this instance, only channel 72c is provided within overmold area 130c. The body 132c of slitter may be provided by a harder material.

Many other configurations for channels and recessed areas are contemplated. In all instances, these structures are adapted to receive a lead or catheter body without actually providing a clamping structure. The thumb of the user accomplishes the retention of the lead or catheter body. Because of the flexibility associated with this retention mechanism, the slitting tool of the current invention can be used with lead and/or catheter bodies having different radial section sizes and shapes. Thus, various versions of the slitter is generally not needed.

Figure 16A:
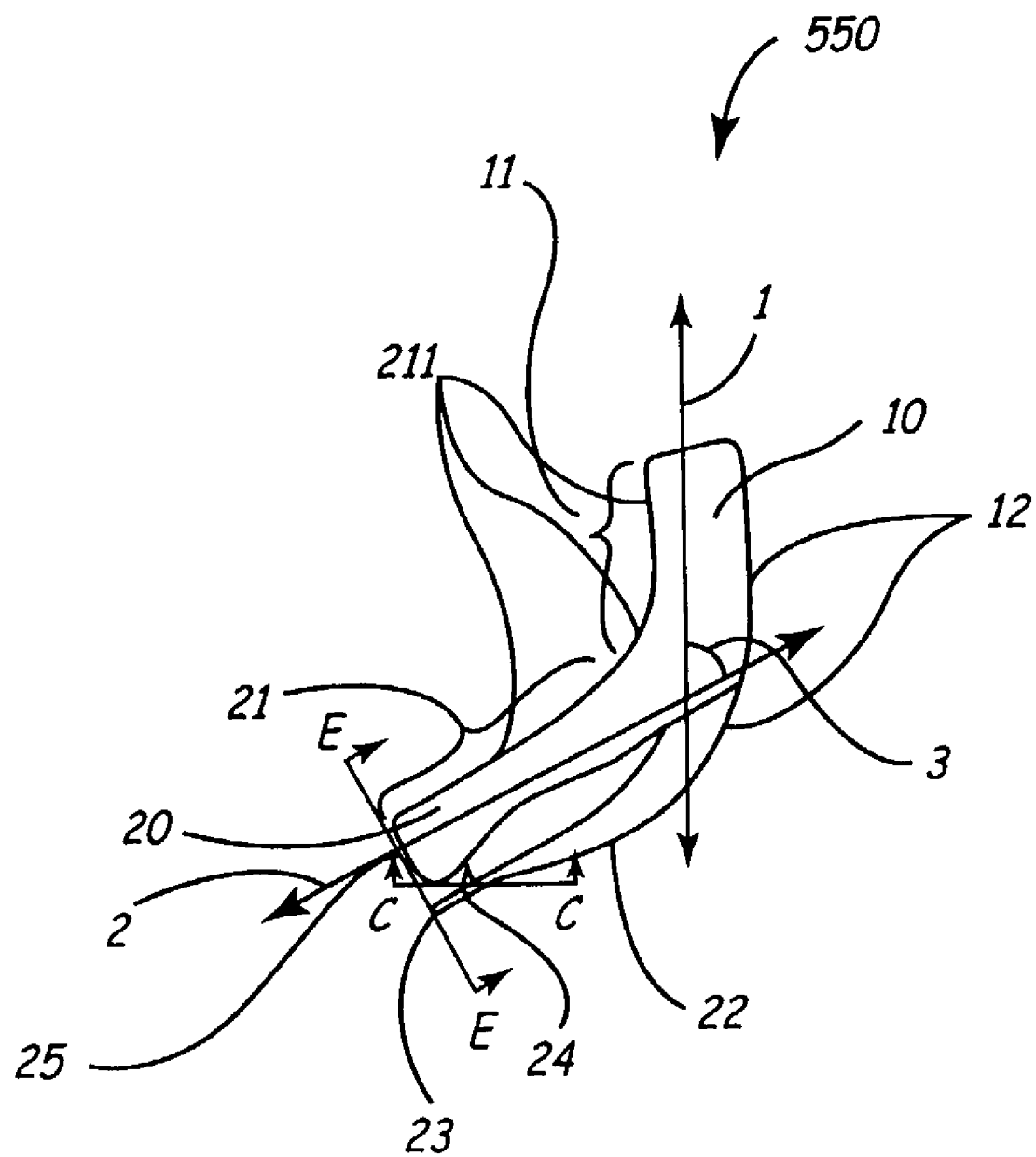
FIG. 16A is a side, plan view of yet another embodiment of a slitting tool according to the present invention.

FIG. 16A is a side, plan view of yet another embodiment of a slitting tool 550 according to the present invention. Slitting tool 550 includes a body portion 10 and a nose portion 20 having an orientation with respect to one another generally the same as body 51 and nose 53 of slitting tool 50 presented in FIG. 3. The orientation is further defined in FIG. 16A by a first axis 1 and a second axis 2, wherein second axis 2, which is substantially aligned along nose portion 20, extends at an angle 3 with respect to first axis 1, which is substantially aligned along body portion 10. According to the present invention, embodiments include angle 3 between approximately 5 degrees and approximately 90 degrees, body portion 10 extending along axis 1 between approximately 1 inch and approximately 2 inches, and nose portion extending along axis 2 between approximately 0.5 inch and approximately 1 inch.

As illustrated in FIG. 16A, body portion 10 includes an inner surface 11 forming a first portion of a gripping zone 211 and an outer surface 12 forming an outer gripping zone. Nose portion 20 includes an inner surface 21 forming a second portion of gripping zone 211, a forward edge 25, a cutting edge 24, a leading edge 23, and a bottom surface 22. (Note that outer surface 12 corresponds to top surface 52 of the alternate embodiment presented in FIG. 3, as bottom surface 22 corresponds to front surface 54 shown in FIG. 3; however inner surfaces 21 and 11 do not correspond to inner surface 56 described for the alternate embodiment depicted in FIG. 3.) According to one embodiment of the present invention, body portion 10 and nose portion 20 are formed as a unitary and continuous part; furthermore cutting edge 24, recessed from forward edge 25 and leading edge 23 and extending between inner surface 21 and bottom surface 22, is formed in nose portion 20 as opposed to being part of a separate cutting member that would be coupled to a nose, such as cutting member 60 described for the alternate embodiment presented in FIG. 3. Slitting tool 550 may be formed by a machining process or a molding process or a combination of both; such processes are known to those skilled in the art. Alternate embodiments are formed from ceramics or metals having minimum hardness properties necessary for forming a cutting edge, for example an equivalent of approximately 34 on a Rockwell C scale. Suitable metal materials are numerous and include, but are not limited to, the following: stainless steel, titanium, steel alloys, and nickel alloys. Furthermore, plating, for example nickel-plating, is formed over the tool for enhanced corrosion resistance in one embodiment of the present invention. In another embodiment according to the present invention, slitting tool 550, formed from a metal, is toughened to enhance cutting edge 24 by means of a surface or subsurface modification process, examples of such processes include ion implantation, nitriding, and carborizing, all well known to those skilled in the art.

According to the present invention, one embodiment of slitting tool 550 is formed by a metal injection molding process followed by a sharpening process for cutting edge 24. Further detail regarding embodiments formed in this manner is presented below in conjunction with FIG. 19.

Figure 16B:
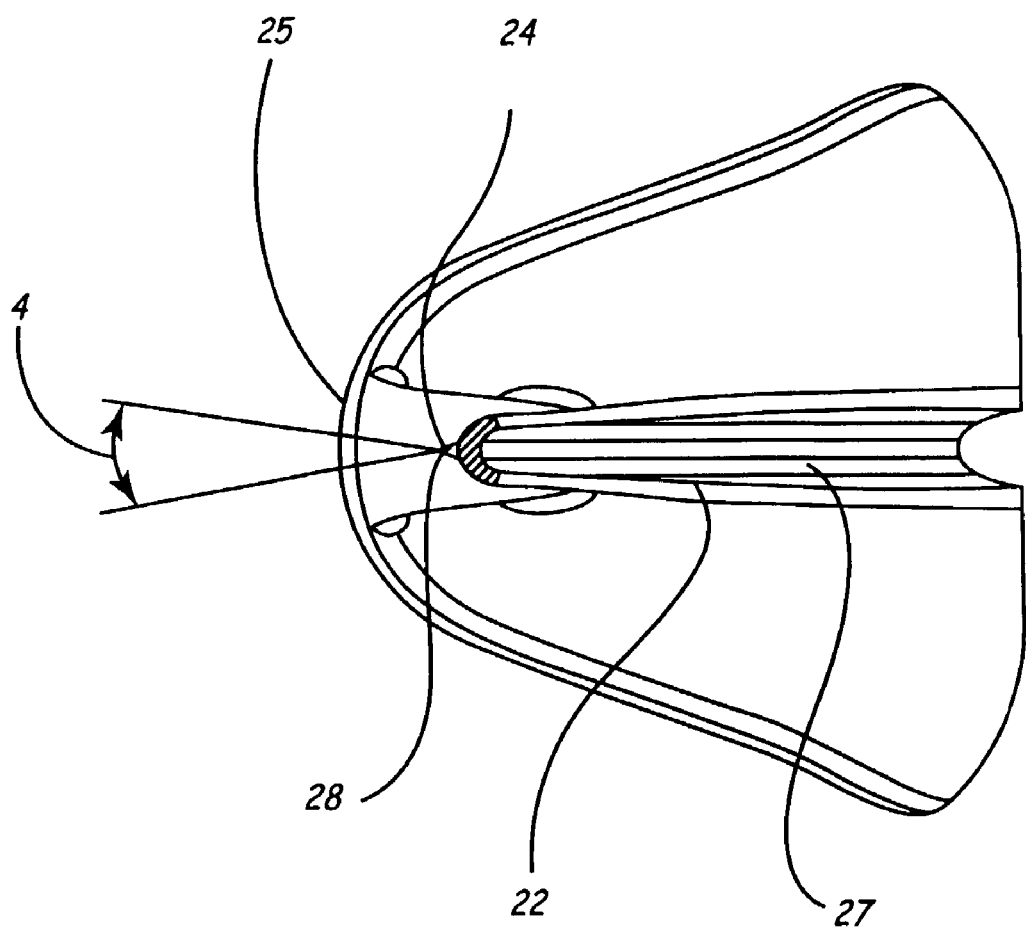
FIG. 16B is a partial section view through a section line of FIG. 16A.

FIG. 16B is a partial section view through section line C-C of FIG. 16A. As illustrated in FIG. 16B, cutting edge 24 is formed by a wedge 28 having an angle 4. According to embodiments of the present invention, angle 4 is between approximately 10 degrees and approximately 50 degrees. FIG. 16B further illustrates bottom surface 22 including a channel 27, according to one embodiment of the present invention. Channel 27 helps to guide a lead or catheter body, such as lead body 521 of FIGS. 1 and 2, along bottom surface 22 to outer surface 12 (FIG. 16A) where it is held against slitting tool 550 in a manner as that illustrated in FIG. 2.

Figure 16C:
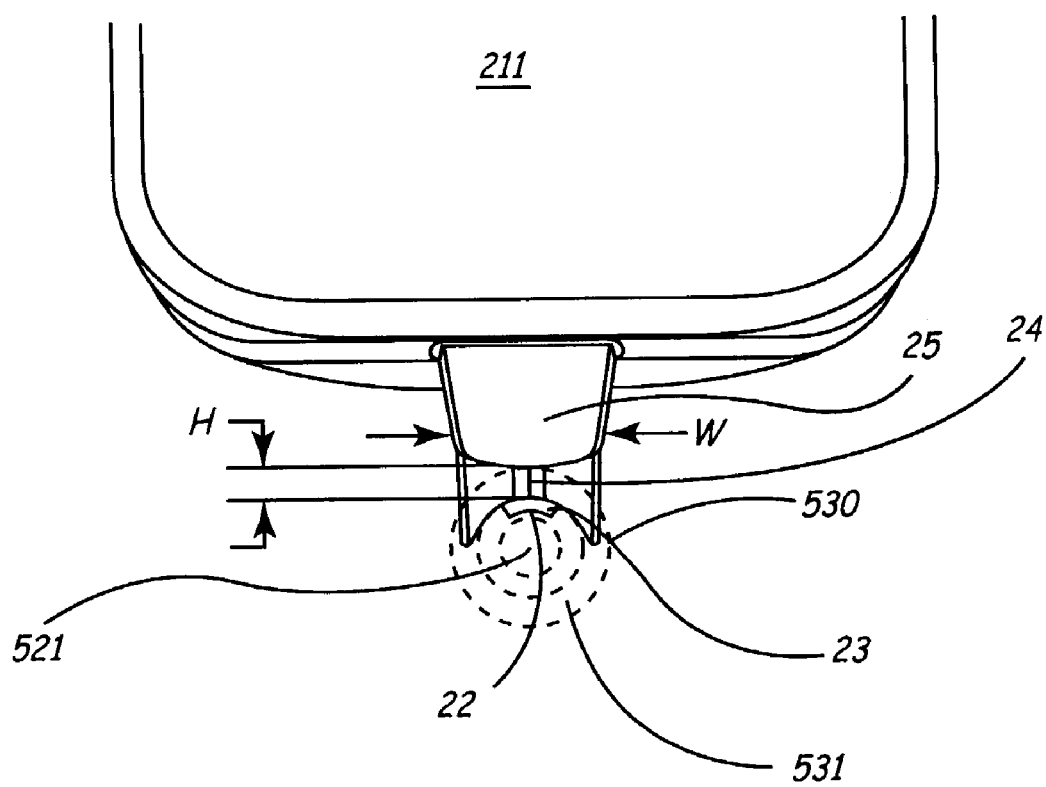
FIG. 16C is a partial section view through a second section line of FIG. 16A.
Figure 16D:
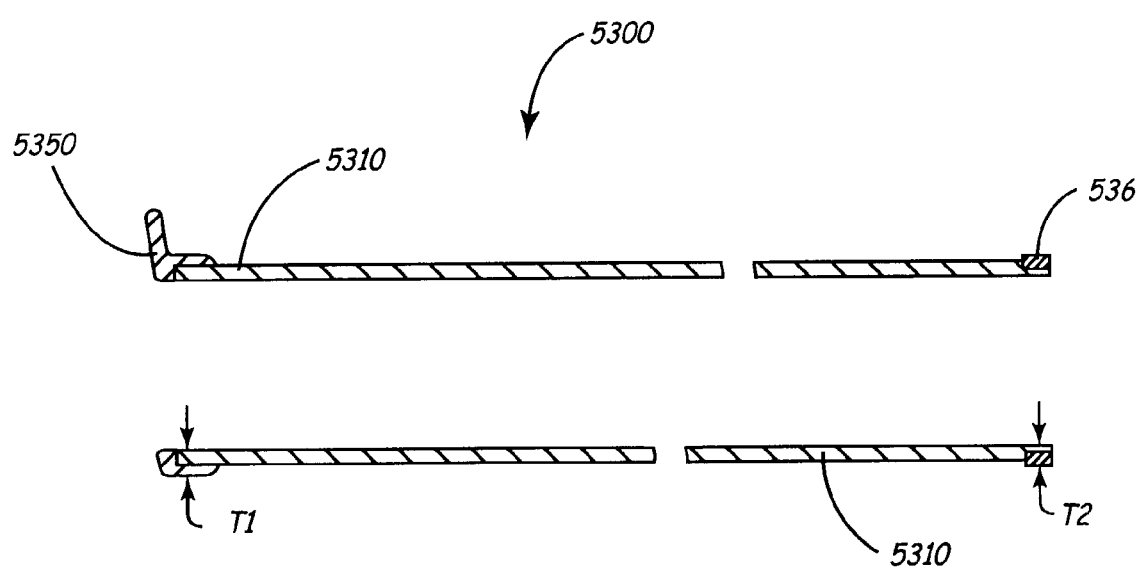
FIG. 16D is a section view of an exemplary delivery sheath.

FIG. 16C is a partial section view through section line E-E of FIG. 16A including dashed lines defining delivery sheath 530 and lead body 521. As illustrated in FIG. 16C, cutting edge 24 has a projected height "H" corresponding to a maximum thickness of delivery sheath wall 531. According to one embodiment of the present invention, height "H" is minimized to approach the maximum thickness of wall 531 thereby reducing a length of cutting edge 24 exposed during slitting in order to minimize a chance of cutting edge 24 coming into contact with lead body 521 if lead body 521 falls away from bottom surface 22. FIG. 16D is a section through an exemplary delivery sheath 5300 illustrating two potential locations for maximum wall thicknesses. A thickness T1 of a wall 5310 of sheath 5300 is located in proximity to a proximal end of sheath where handle 5350 is formed, and a thickness T2 of wall 5310 of sheath 5300 is located in proximity to a distal end where a radiopaque marker or an electrode 536 is formed. A maximum thickness, defined by T1 or T2 or any other segment of wall 5310 will dictate a minimum cutting edge height "H" according to one embodiment of the present invention. According to another embodiment, height "H" of cutting edge is between approximately 0.010 inch and approximately 0.060 inch. As further illustrated in FIG. 16C, a forward edge 25 is in close proximity to sheath wall 531 during slitting. According to one embodiment of the present invention, forward edge 25 serves to keep cutting edge 24 stable during slitting by limiting height "H", as previously described, but also includes a width "W" which is minimized to reduce a drag of forward edge 25 as it travels along an outer surface of sheath wall 531 during slitting. According to one embodiment width "W" is between approximately 0.06 inch and approximately 0.20 inch. Furthermore, as illustrated in FIG. 16C, leading edge 23 forms a low-profile section for insertion between lead body 521 and delivery sheath wall 531 orienting cutting edge 24 to slit delivery sheath wall 531 and keeping slitter 550 tracking within sheath 530.

Figure 17A:
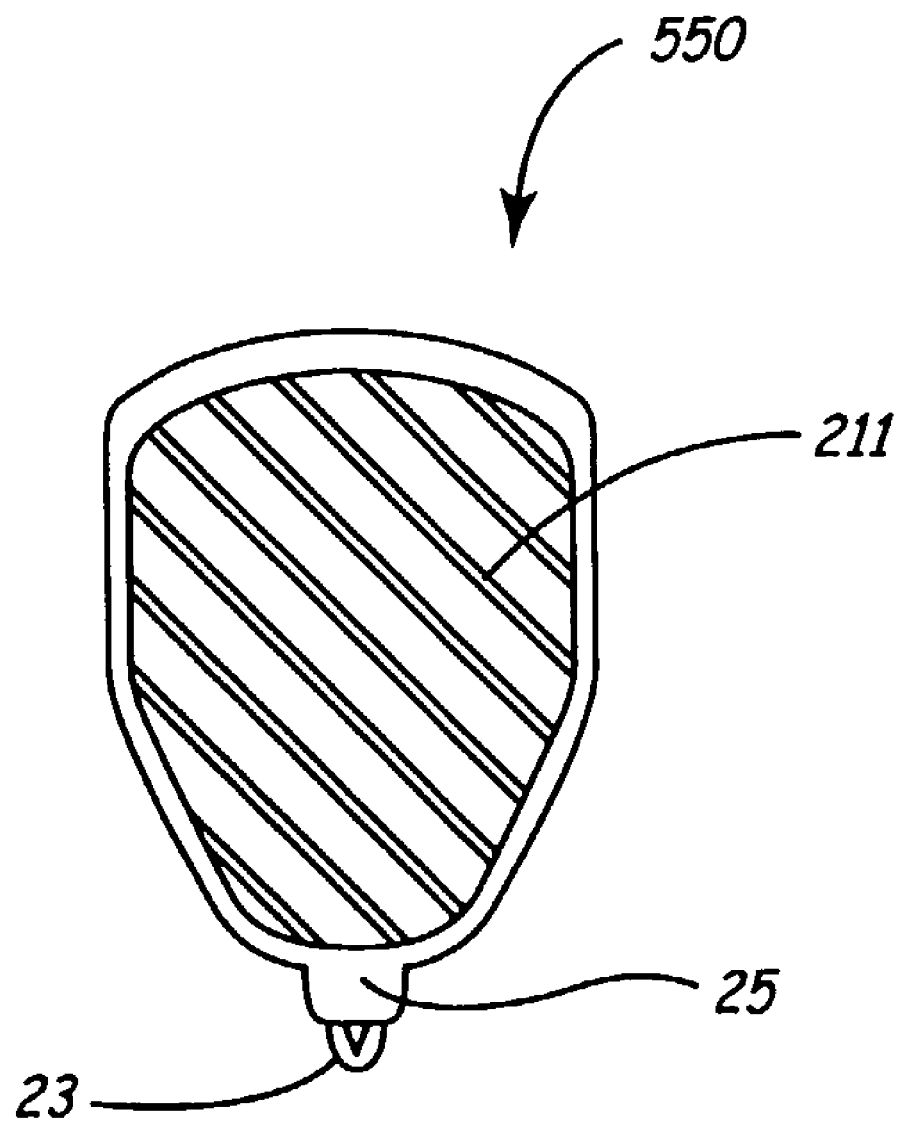
FIG. 17A is a front plan view of the slitting tool of FIG. 16A.

FIG. 17A is a front plan view of slitting tool 550 of FIG. 16A. As illustrated in FIG. 17A, and according to one embodiment of the present invention, inner surface 211 is textured for enhanced gripping. Alternate means for texturing inner surface 211 are described in conjunction with FIG. 4A. In alternate embodiments according to the present invention inner surface 211 is enhanced for gripping by means of an oveilay material, furthermore an alternate embodiment includes only a select zone of inner surface 211, located along body portion 10, enhanced for gripping.

Figure 17B:
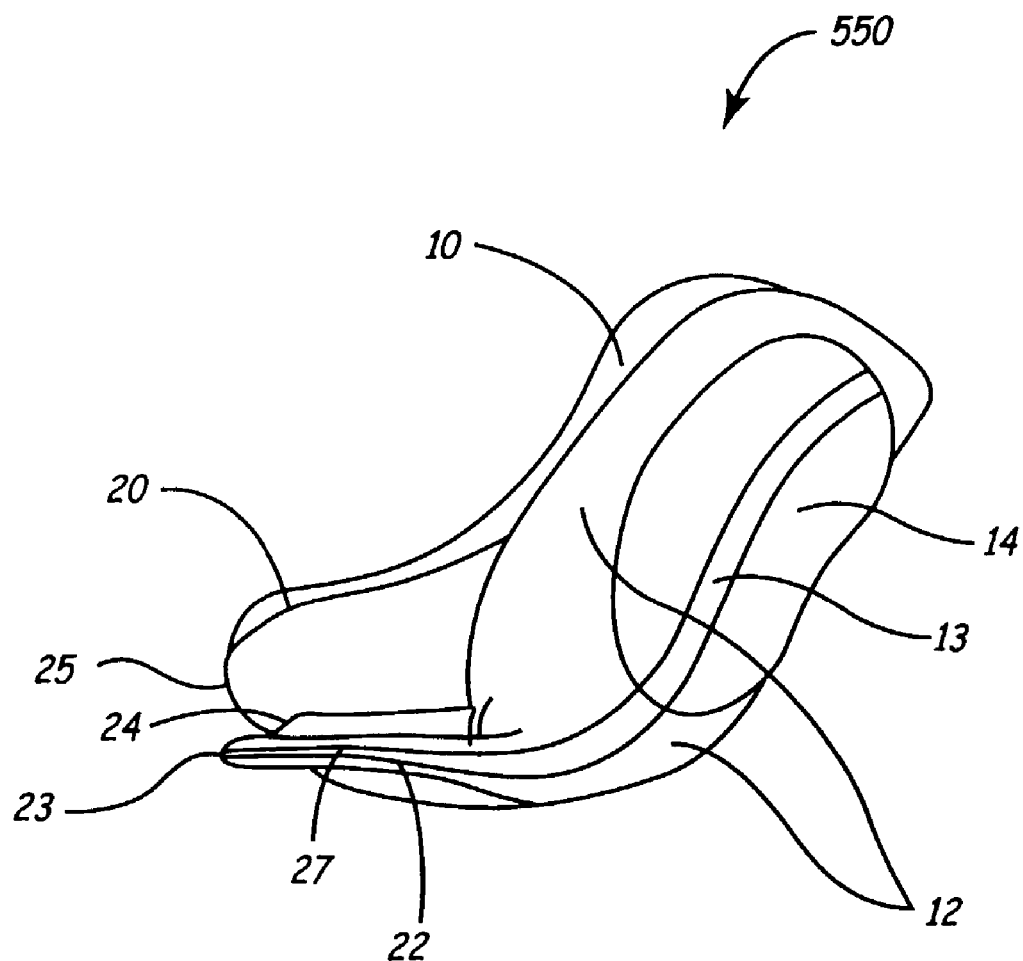
FIG. 17B is a perspective view of the slitting tool of FIG. 16A.

FIG. 17B is a perspective view of slitting tool 550 of FIG. 16A oriented to show additional features according to alternate embodiments of the present invention. As illustrated in FIG. 17B, outer surface 12 of body portion 10 includes a recessed area 14 wherein a thumb, for example, may rest when slitting tool 550 is gripped. In an alternate embodiment according to the present invention recess 14 is not provided. As further illustrated in FIG. 17B, channels 27 extends along bottom surface 23 of nose portion 20 to join a second channel 13 formed along outer surface 12 of body portion 10, According to one embodiment of the present invention, channels 27 and 13 are provided to guide a lead body, such as lead body 521 illustrated in FIGS. 1 and 2, when slitting tool 550 is grasped for slitting a delivery sheath wall, such as delivery sheath wall 531 also illustrated in FIGS. 1 and 2. In alternate embodiments channels 27 and 13 may be discrete, for example not joined as illustrated in FIG. 17B, and one channel, either 27 or 13 is provided while the other is not. Furthermore, alternate embodiments include channels 27 and, or 13 having surfaces, as described herein for channel 72 introduced in FIG. 4A, enhanced for gripping a lead body, such as lead body 521 shown in FIGS. 1 and 2, and having various cross-sections such as channels 72, 72a, 72b, and 72c described in conjunction with FIGS. 12-15.

Figure 18:
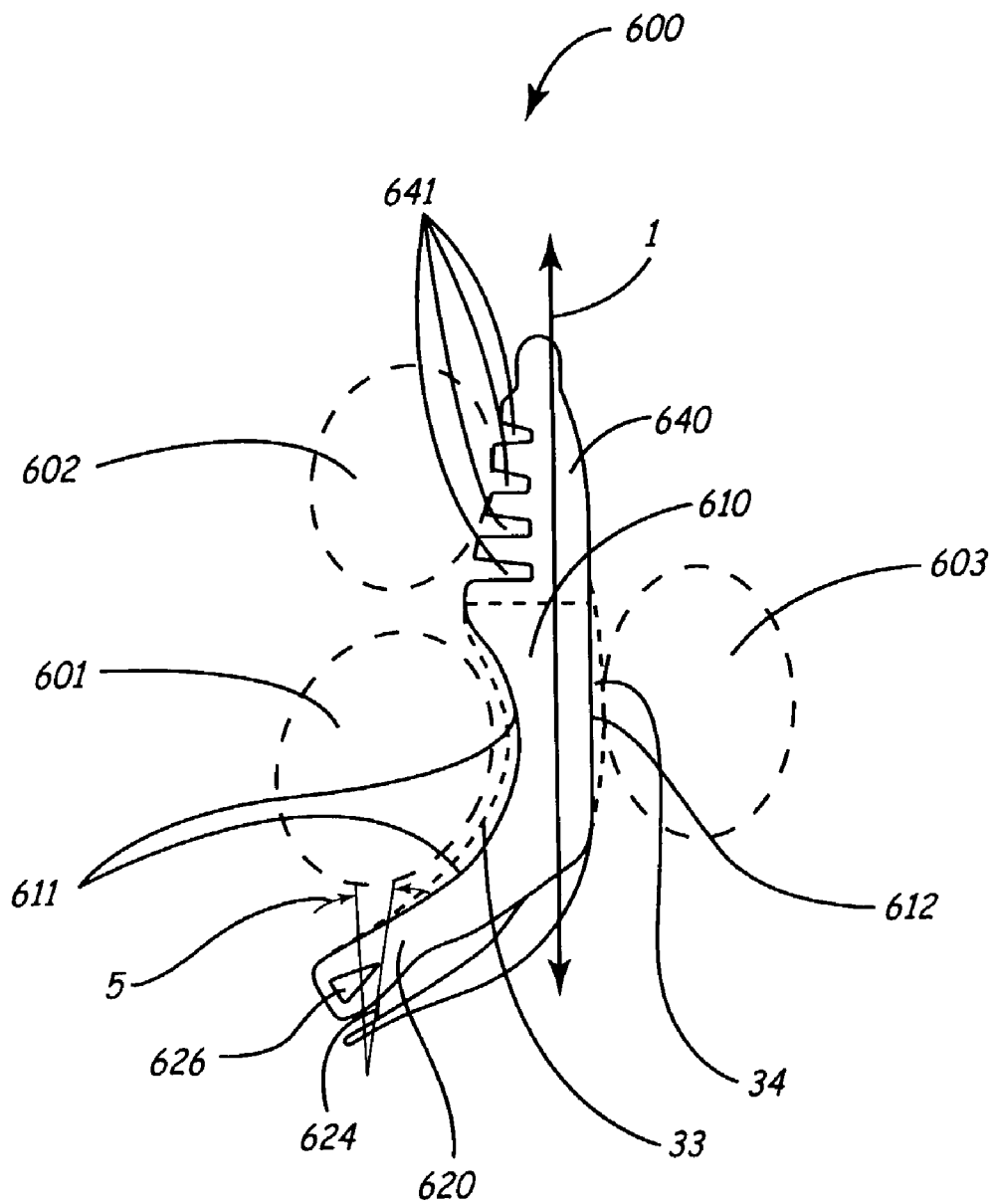
FIG. 18 is a side plan view of another embodiment according to the present invention.

FIG. 18 is a side, plan view of another embodiment according to the present invention including dashed lines representing a first finger 601, a second finger 602, and a thumb 603. As illustrated in FIG. 18, a slitting tool 600 includes a body portion 610 and a nose portion 620 oriented with respect to one another as body portion 10 and nose portion 20 shown in FIG. 16A. Slitting tool 600 further includes a tail portion 640, substantially aligned with body portion 610 along first axis 1. According to one embodiment of the present invention, tail portion 640 adds a weight, to balance a weight of nose portion 620, and provides a surface along which second finger 602 rests in proximity to first finger 601 so that second finger 602, in concert with first finger 601 and thumb 603 may hold slitting tool 600 stable during slitting. According to the present invention, body portion 610, in conjunction with tail portion 640, extend along axis 1 between approximately 1 inch and approximately 2 inches. FIG. 18 also depicts a cutting edge 624, similar to cutting edge 24 previously described, at an angle 5 to an axis parallel with axis 1. According to an embodiment of the present invention, angle 5 is between approximately 5 degrees and approximately 70 degrees.

As further illustrated in FIG. 18, in one embodiment according to the present invention, slitting tool 600 includes cut out features 641 and 626 in order to conserve material, reduce weight, reduce wall thickness, and/or provide decorative embellishment. Features 641 may also serve to enhance gripping of slitting tool 600. As further illustrated with dashed lines in FIG. 18, a polymer overlay 33, covering all or a portion of inner surface 611, and a polymer overlay 34, covering all or a portion of outer surface 612, are included to enhance gripping of slitting tool 600 according to another embodiment of the present invention. In alternate embodiments only one of the overlays 33, 34 is included. In alternate embodiments overlays 33 and/or 34 are formed from any of the materials described herein above as a tacky overmolding material or from any elastomeric material, an example of which is santoprene.

Figure 19:
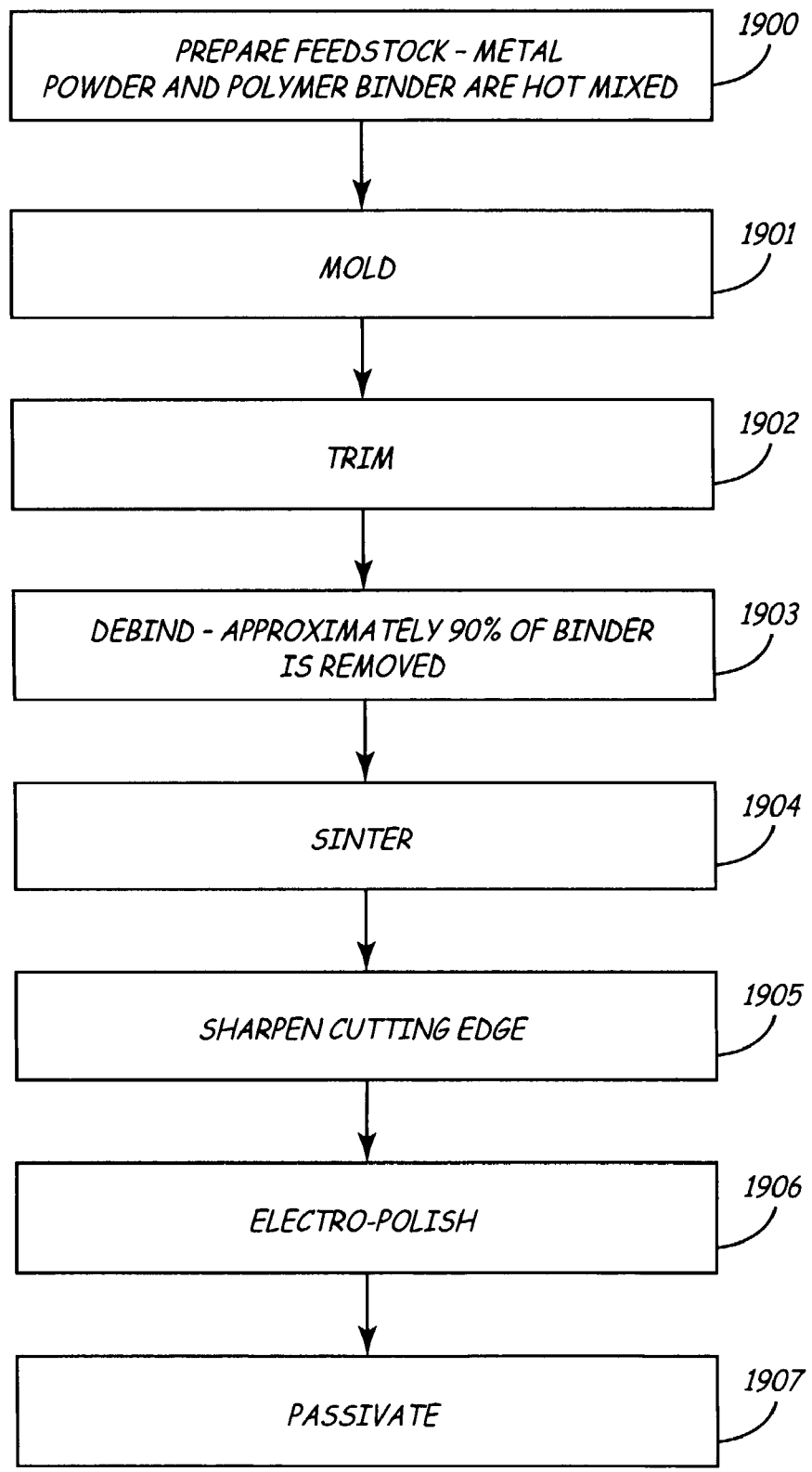
FIG. 19 is a flow chart illustrating one process for forming a slitting tool.

FIG. 19 is a flow chart illustrating one process for forming a slitting tool. According to embodiments of the present invention, metal injection molding, or MIM, is used to form a slitting tool, such as slitting tools 500, 550, and 600 described herein. The MIM process is capable of forming metals into complex shapes including thin wall sections that may be difficult to achieve with machining processes. Suitable metal materials from which a slitting tool may molded include stainless steel, titanium, steel alloys, and nickel alloys. A metal powder mixed with a polymer binder forms the raw material, or feedstock, for molding (1900). An example of such a material is Catamold® 17-PH, ready-to-mold granules including stainless steel, available from BASF at 67056 Ludwigahafen, Germany. Injection molding (1901) is accomplished using tooling and methods know by those skilled in the art of MIM. Following injection molding, gates and/or flash is trimmed (1902) from slitting tool parts prior to placing the parts in a debind oven. According to one embodiment a debinding process (1903) occurs at temperatures below the softening point of the binder by including a catalyst; the process removes approximately 90% of the polymer binder from the molded part. Once debinded, slitting tool parts are sintered (1904) using a temperature and atmosphere and profile suitable to the alloy being processed. Sintering, the fusion and bonding of neighboring particles one to another at an elevated temperatures bringing the structure of the part together and reducing porosity, is a process known to those skilled in the art. Referring to FIG. 19, cut out features 641 illustrated therein, according to one embodiment of the present invention, serve to reduce wall thicknesses in tail 640 to prevent sink, or deformation, during cooling following sintering. Cutting edges, such as cutting edge 24 described herein, of slitting tool parts are sharpened (1905) following sintering. According to embodiments of the present invention, sharpening may be accomplished by grinding, wire EDM, or chemical milling methods, all of which are known to those skilled in the art Referring to FIG. 16B, wedge 28, as molded, would have an angle greater than angle 4 that is reduced via sharpening to form cutting edge 24. Final steps of electropolishing (1906) and passivation (1907) are optional according to the present invention. In one embodiment, electropolishing is performed to enhance cutting edge sharpness. Furthermore, in alternative embodiments according to the present invention, MIM slitting tool parts are toughened prior to sharpening by surface or sub-surface modification techniques well know to those skilled in the art, for example by ion implantation, nitriding, or carborizing.

Figure 20A:
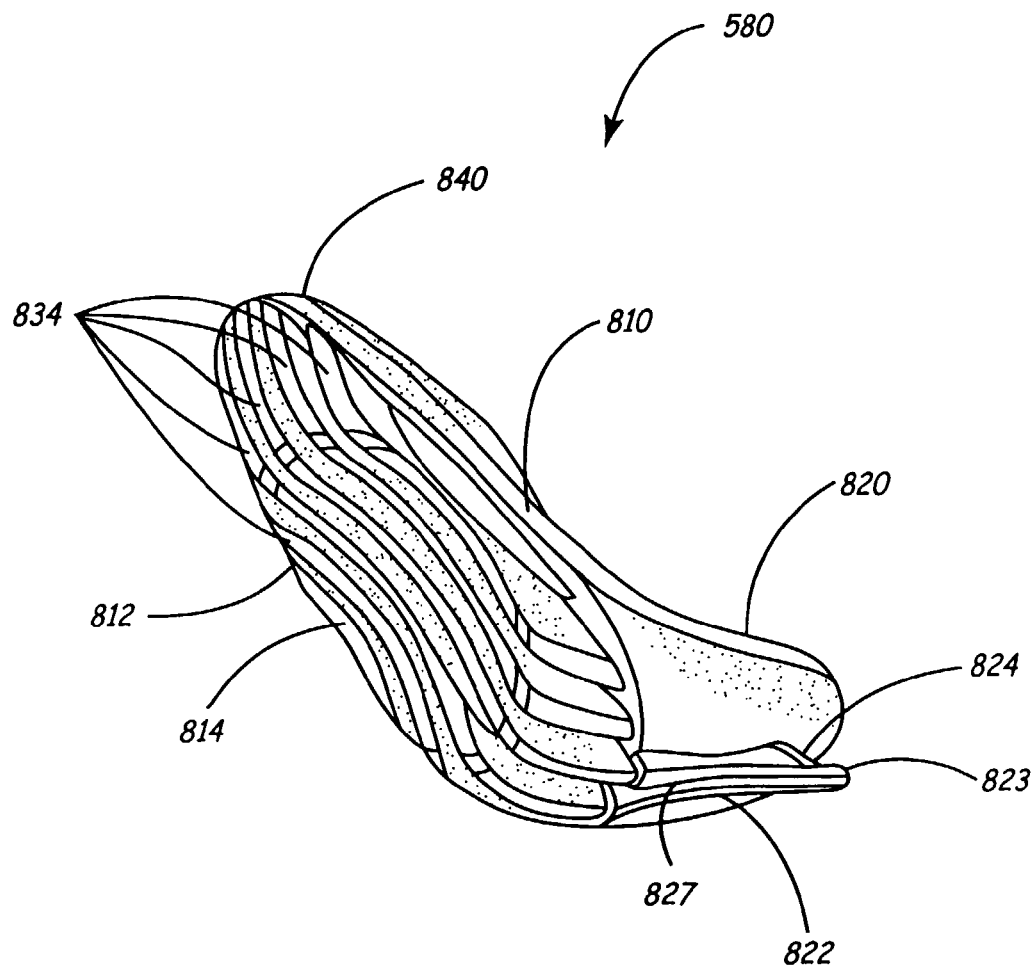
FIG. 20A is a perspective view an alternate embodiment of a slitting tool.
Figure 20B:
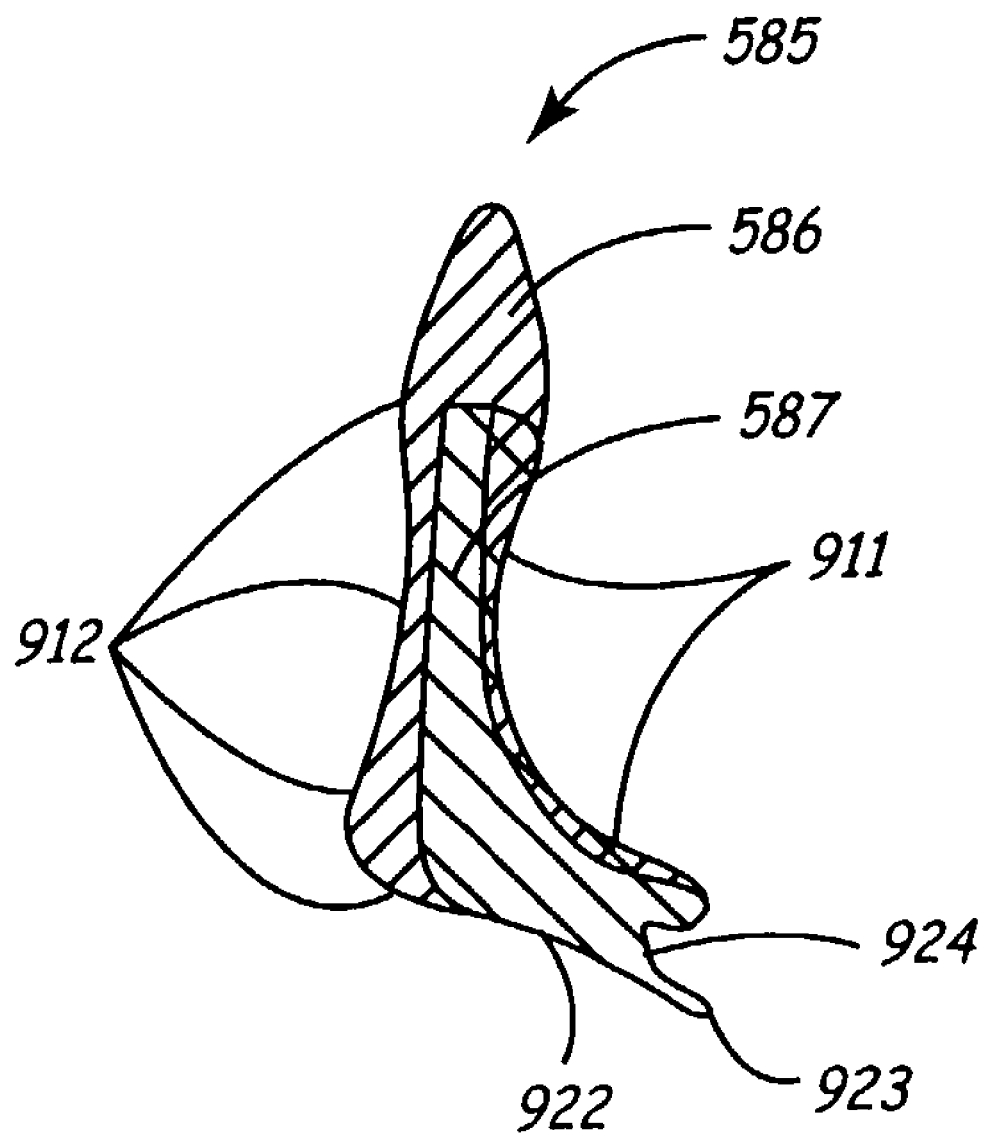
FIG. 20B is a section side view of another embodiment of a slitting tool.

FIG. 20A is a perspective view an alternate embodiment of a slitting tool 580. As illustrated in FIG. 20A, slitting tool 580 includes a nose portion 820, a body portion 810, and a tail portion 840, wherein an outer surface 812 of body portion 810 is formed with a recess 814 and ridges 834 running parallel to an axis of body 810, for example first axis 1 as illustrated in FIGS. 16A and 18, as illustrated, or running perpendicular to the axis. As further illustrated in FIG. 20A, nose portion 820 includes a cutting edge 824 a leading edge 823 and channel 827, which is formed along a bottom surface 822 of nose portion 820. According to one embodiment of the present invention, slitting tool 580 may be formed as a unitary and continuous part by machining or injection molding, as described above, however in an alternate embodiment ridges 834 reference F are part of an over-molded shell as illustrated in FIG. 20B. FIG. 20B is a section side view of a slitting tool 585 including a core 587 captured within an over-molded shell 586. As illustrated in FIG. 20B, core 587 includes a cutting edge 924, a leading edge 923, and a bottom surface 922, while shell 586 forms an inner surface 911 and an outer surface 912 which are surfaces designed to be grasped by a user as illustrated in FIGS. 1 and 2. In an alternate embodiment, inner surface 911 is formed by core 587 (as indicated by overlapping crosshatching). In various embodiments, core 587 is formed from a metal or ceramic and over-molded shell 586 is formed from any of the materials described herein above as a tacky overmolding material or from a harder plastic such as ABS or polycarbonate or a combination thereof. Core may be molded, for example by MIM as described above, or machined.

Figure 21:
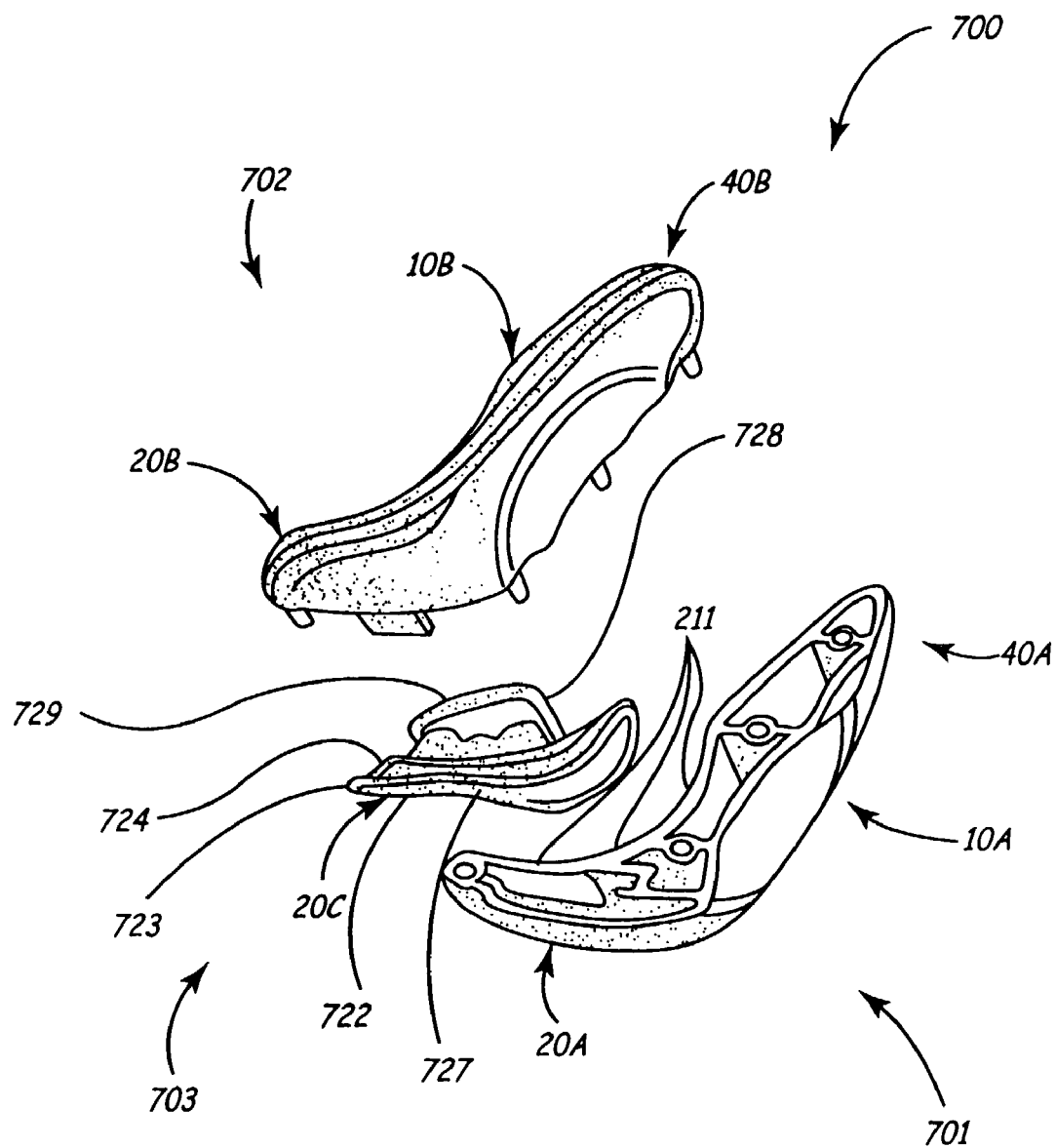
FIG. 21 is an exploded perspective view of yet another embodiment according to the present invention.

FIG. 21 is an exploded perspective view of yet another embodiment according to the present invention. As illustrated in FIG. 21, a slitting tool 700 is formed from three pieces: first shell 701, second shell 702, and captured component 703. First shell 701 includes a first part of body portion 10A, a first part of nose portion 20A, and first part of tail portion 40A, while second shell includes a second part of body, nose, and tail, 10B, 20B, and 40B, respectively. As illustrated in FIG. 21 first shell 701 and second shell 702 press fit together around captured component 703, such that captured component 703 forms a third part of nose portion 20C including a cutting edge 724, a leading edge 723, and a bottom surface 722 which includes a channel 727. In alternate embodiments, shells 702 and 703 may be snap fit together, welded together, bonded together, or any combination thereof. When the three pieces are put together, an extension 728 of captured component 703 helps to hold captured component 703 in place so that slitting tool 700 takes on a form very similar to those illustrated in FIGS. 16A, 17B, and 18. According to embodiments of the present invention captured component 703 is formed from a metal or a ceramic and is either machined or molded as previously described, while first shell 701 and second shell 702 are molded from a hard plastic, such as ABS or polycarbonate or a combination thereof. As illustrated in FIG. 21, extension 728 includes a flat surface 729 (directed into the page) which, according to a MIM embodiment of captured component 703, provides a surface on which captured component 703 rests in a sintering oven; additionally, flat surface 729 may provide a key datum surface for secondary operations on and inspection of captured component 703.

Figure 22:
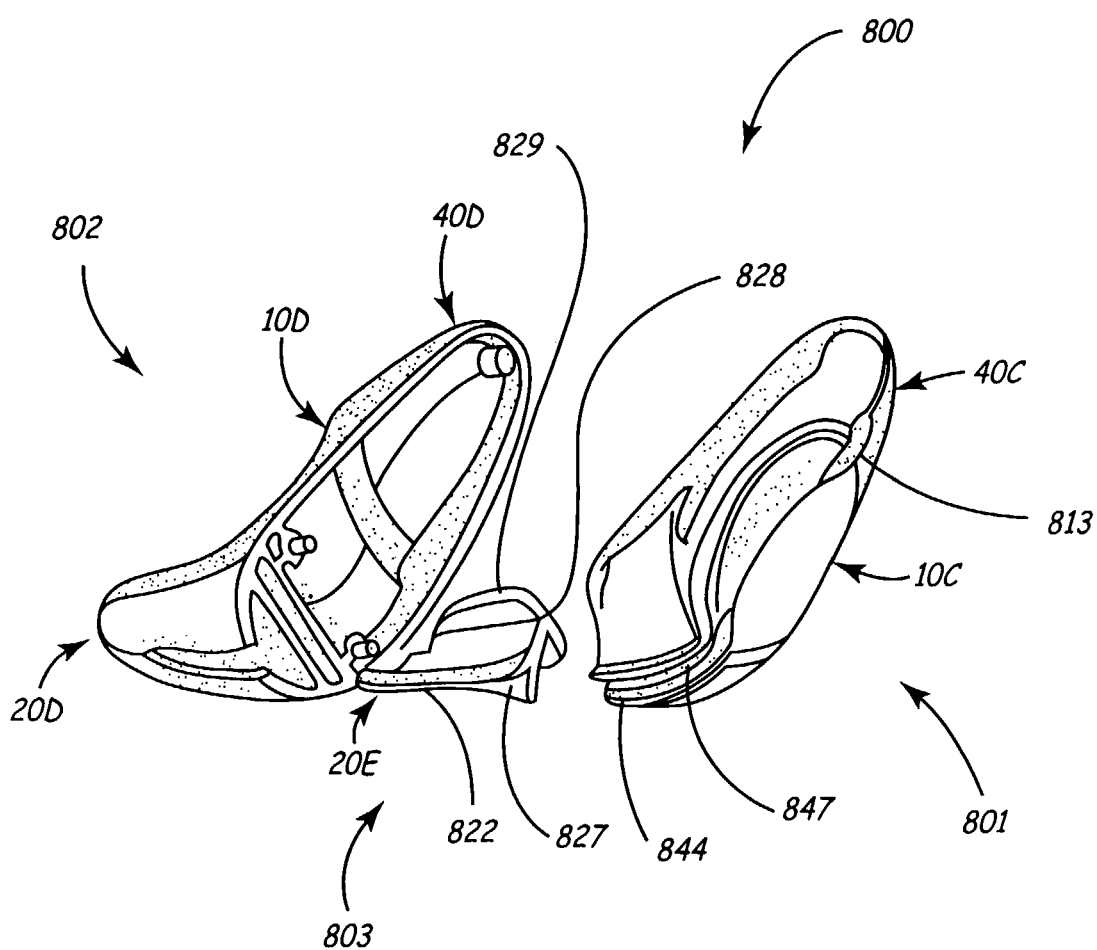
FIG. 22 is an exploded perspective view of another embodiment according to the present invention.

FIG. 22 is an exploded perspective view of another embodiment according to the present invention. As illustrated in FIG. 22, a slitting tool 800 is formed from three pieces: first shell 801, second shell 802, and captured component 803. First shell 801 includes a first part of body portion 10C, a first part of nose portion 20C, and first part of tail portion 40C, while second shell includes a second part of body, nose, and tail, 10D, 20D, and 40D, respectively. As illustrated in FIG. 22 first shell 801 and second shell 802 press fit together around captured component 803, such that captured component 803 forms a third part of nose portion 20E including a cutting edge 824, a leading edge 823, and a bottom surface 822 which includes a channel 827. In alternate embodiments, shells 802 and 803 may be snap fit together, welded together, bonded together, or any combination thereof. When the three pieces are put together, an extension 828 of captured component 803 helps to hold captured component 803 in place so that slitting tool 800 takes on a form very similar to those illustrated in FIGS. 16A, 17B, and 18; furthermore bottom surface 822 and channel 827 of captured component are extended by a second part of bottom surface 844 and a second part of channel 847 included in first shell 801. As further illustrated in FIG. 22, first shell includes a second channel 813 independent of first channel 827, 847 as an alternate embodiment to a continuous channel formed by channels 27 and 13 illustrated in FIG. 17B. According to embodiments of the present invention captured component 803 is formed from a metal or a ceramic and is either machined or molded as previously described, while first shell 801 and second shell 802 are molded from a hard plastic, such as ABS or polycarbonate or a combination thereof. As illustrated in FIG. 22, extension 828 includes a flat surface 829 (directed into the page) which, according to a MIM embodiment of captured component 803, provides a surface on which captured component 803 rests in a sintering oven; additionally, flat surface 829 may provide a key datum surface for secondary operations on and inspection of captured component 803.

EXAMPLES

Figure 23:
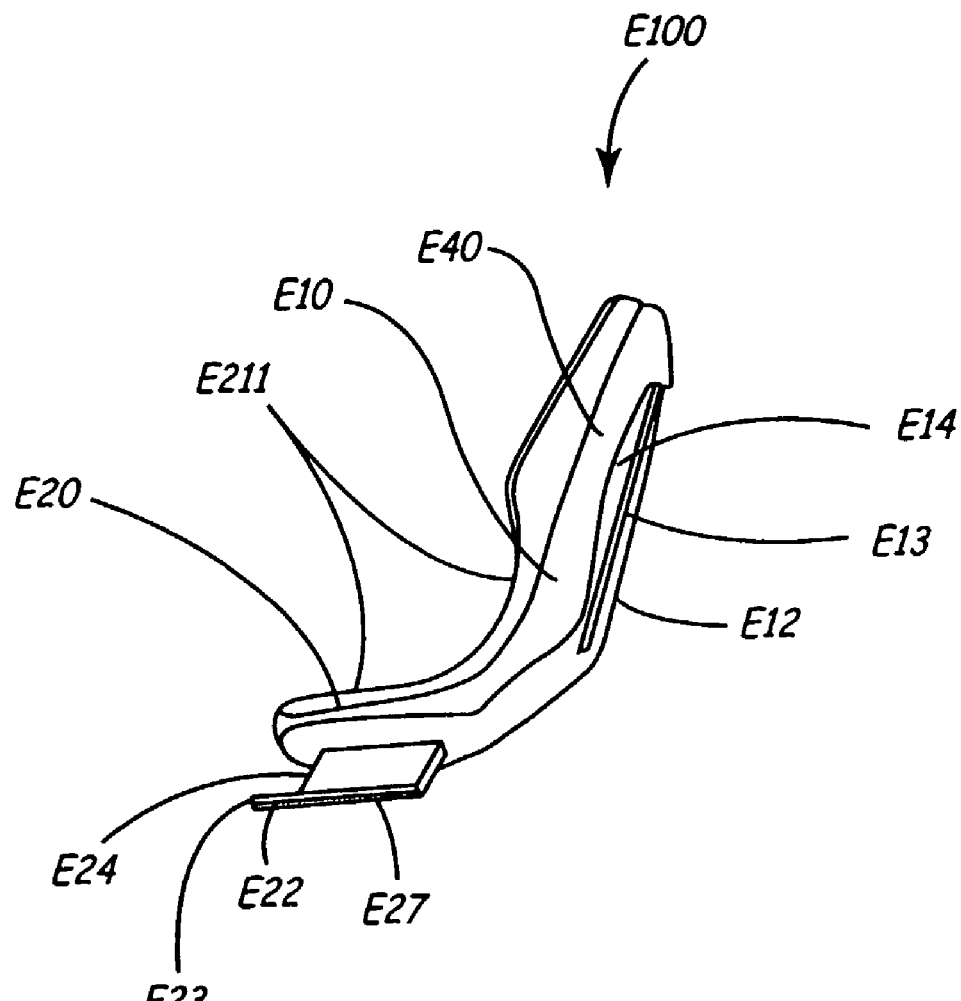
FIG. 23 is a perspective view of an alternate embodiment of a slitting tool according to the present invention.

Slitting tools were made from 420 stainless steel having a form illustrated in FIG. 23. FIG. 23 is a perspective view of a slitting tool E100 including a body portion E10, a nose portion E20, and a tail portion E40. As illustrated in FIG. 23, body portion E10 includes a first portion of inner gripping zone E211, and an outer surface E12 including a recessed area E14 and a channel E13. As further illustrated in FIG. 23, nose portion E20 includes a second portion of inner gripping zone E211, a cutting edge E24 recessed from a leading edge E23, and a bottom surface E22 including a channel E27. Slitting tools made according to the embodiment illustrated in FIG. 23 were tested to determine average slitting forces through a Medtronic model 6218 Attain catheter wall constructed from a stainless steel braid-reinforced polyamide. The results of the testing, in grams, are presented in the table below. Each of the slitting tools tested had a cutting edge height of approximately 0.12 inch, the height defined as illustrated in FIG. 16C; and the wedge angle of each slitting tool, presented in the table below, is defined as illustrated in FIG. 16B.

|  | 10 degree wedge angle (Ground cutting edge) | 20 degree wedge angle (EDM'ed cutting edge) | 40 degree wedge angle (Ground cutting edge) |
| --- | --- | --- | --- |
| Run 1 | 519 | 545 | 504 |
| Run 2 | 503 | 572 | 573 |

Finally, it will be appreciated by those skilled in the art that numerous variations and modifications of the described embodiments may be made. Hence, descriptions of particular embodiments provided herein are intended as exemplary, not limiting, with regard to the following claims.

The invention claimed is:

1. A slitting tool for severing a tubular body positioned over a lead, comprising:
   a body portion extending along a first axis and including means for gripping by a hand of a user, the means for gripping extending substantially along a first plane; and
   a nose portion extending along a second axis and including means for severing the tubular body, the means for severing extending substantially along a second plane perpendicular to the first plane and being recessed from a leading edge of the nose portion, wherein the second axis extends at an angle between approximately 5 degrees and approximately 90 degrees with respect to the first axis.

2. A slitting tool, comprising:
   a body portion oriented along a first axis and including an inner surface forming an inner gripping zone on a front side of the body portion and an outer surface forming an outer gripping zone on a back side of the body portion, the inner and outer surfaces of the body portion being in a lateral plane;
   a nose portion joined to the body portion to extend from the front side of the body portion, the nose portion oriented along a second axis, and including a top surface, a bottom outer surface, a leading edge terminating the bottom surface, and a cutting edge recessed from the leading edge, wherein the second axis extends at an angle between approximately 5 degrees and approximately 90 degrees with respect to the first axis and wherein the cutting edge extends in a plane that is substantially perpendicular to the lateral plane of the inner and outer surfaces of the body portion.

3. The slitting tool of claim 2, wherein the cutting edge is formed by a wedge and extends from the leading edge toward the inner surface of the nose portion.

4. The slitting tool of claim 3, wherein, to form the cutting edge, the wedge is sharpened by a process selected from the group comprising grinding, chemical milling, and wire EDM.

5. The slitting tool of claim 3, wherein the wedge has an angle between approximately 10 degrees and approximately 50 degrees.

6. The slitting tool of claim 3, wherein the cutting edge extends at an angle from the first axis, the angle between approximately 5 degrees and 70 degrees.

7. The slitting tool of claim 2, wherein the outer gripping zone includes a first channel adapted to engage a lead body.

8. The slitting tool of claim 7, wherein the bottom outer surface of the nose portion includes a second channel in communication with the first channel to receive the lead body, the second channel starting in proximity to the leading edge and extending toward the body portion.

9. The slitting tool of claim 2, wherein the outer gripping zone includes a recessed area.

10. The slitting tool of claim 2, wherein the bottom surface of the nose portion includes a channel starting in proximity to the leading edge and extends along a length of the outer surface of the body portion.

11. The slitting tool of claim 2, wherein the nose portion further includes a forward edge terminating the inner surface of the nose portion and extending toward the bottom surface to limit a height of the cutting edge, the cutting edge recessed from the forward edge.

12. The slitting tool of claim 2, further comprising a tail portion, the tail portion joined to the body portion and substantially aligned with the body portion.

13. The slitting tool of claim 2, wherein the inner gripping zone includes a textured surface.

14. The slitting tool of claim 2, wherein the outer gripping zone includes a textured surface.

15. The slitting tool of claim 2, wherein the unitary member is comprised of a material selected from the group consisting of stainless steel, titanium, nickel alloys, and steel alloys.

16. The slitting tool of claim 15, wherein the unitary member is formed by a machining process.

17. The slitting tool of claim 15, wherein the unitary member is formed by an injection molding process.

18. The slitting tool of claim 15, wherein all or a portion of the unitary member is toughened by a surface or subsurface modification technique selected from the group comprising ion implantation, nitriding, and carborizing.

19. The slitting tool of claim 15, wherein the cutting edge is sharpened by a secondary process selected from the group comprising grinding, chemical milling, and wire EDM.

20. A slitting tool, comprising:
   an inner gripping zone;
   an outer gripping zone including a recessed area;
   a body portion extending along a first axis and including an inner surface forming a first portion of the inner gripping zone and an outer surface forming the outer gripping zone, the inner and outer surfaces being oriented in a first plane; and
   a nose portion joined to the body portion, extending along a second axis, and including a bottom outer surface, a leading edge, a cutting edge, a forward edge, and an inner surface, the inner surface forming a second portion of the inner gripping zone; wherein, the second axis extends at an angle between approximately 5 degrees and approximately 90 degrees with respect to the first axis, the bottom outer surface includes a channel starting in proximity to the leading edge and extending toward the body portion, the leading edge terminates the bottom surface, and the cutting edge, recessed from the leading edge and the forward edge, is formed by a wedge extending from the leading edge toward the inner surface of the nose portion, and wherein the body portion and the nose portion are formed as a unitary non-hinging member and wherein the cutting edge extends substantially along a second plane perpendicular to the first plane.

21. A slitting tool for severing a tubular body positioned about a lead, comprising:
- a body portion having an outer surface and extending along a first axis, the outer surface forming a gripping area for receiving a thumb of a user and an elongated channel for receiving the lead extending within the gripping area;
- a nose portion extending along a second axis different from the first axis; and
- a cutting edge formed in the nose portion and recessed from a leading edge terminating the nose portion, wherein the gripping area extends laterally in a direction perpendicular to the second axis.

* * * * *